(12) United States Patent
Turner et al.

(10) Patent No.: US 12,134,613 B2
(45) Date of Patent: Nov. 5, 2024

(54) METHOD FOR THE MANUFACTURE OF 3-[(1S)-1-IMIDAZO[1,2-A]PYRIDIN-6-YLETHYL]-5-(1-METHYLPYRAZOL-4-YL)TRIAZOLO[4,5-B]PYRAZINE AND POLYMORPHIC FORMS THEREOF

(71) Applicants: AstraZeneca AB, Sodertalje (SE); Hutchison Medipharma Limited, Shanghai (CN)

(72) Inventors: Andrew Roy Turner, Macclesfield (GB); Andrew Timothy Turner, Macclesfield (GB); Gareth Paul Howell, Macclesfield (GB); Malcolm Allan Young Gall, Cambridge (GB); Keith Raymond Mulholland, Cambridge (GB); Neil Keith Adlington, Cambridge (GB); Zhenping Tian, Shandong (CN); Bo Liu, Shanghai (CN); Qisun Gong, Shanghai (CN); Wei Yu, Shanghai (CN)

(73) Assignees: AstraZeneca AB, Sodertalje (SE); Hutchison Medipharma Limited, Shanghai (CN)

( * ) Notice: Subject to any disclaimer, the term of this patent is extended or adjusted under 35 U.S.C. 154(b) by 619 days.

(21) Appl. No.: 17/274,820

(22) PCT Filed: Sep. 10, 2019

(86) PCT No.: PCT/EP2019/074083
§ 371 (c)(1),
(2) Date: Mar. 10, 2021

(87) PCT Pub. No.: WO2020/053198
PCT Pub. Date: Mar. 19, 2020

(65) Prior Publication Data
US 2022/0048904 A1    Feb. 17, 2022

(30) Foreign Application Priority Data

Sep. 11, 2018  (WO) ................ PCT/CN2018/104941

(51) Int. Cl.
*C07D 471/04*    (2006.01)
(52) U.S. Cl.
CPC .................................. *C07D 471/04* (2013.01)
(58) Field of Classification Search
CPC .. C07D 471/04; C07D 519/00; C07D 487/04; A61K 31/4985
(Continued)

(56) References Cited

FOREIGN PATENT DOCUMENTS

WO    2011/079804 A1    7/2011

OTHER PUBLICATIONS

Berge et al ,Journal of Pharmaceutical of Science, Jan. 1977,66(No. 1), p. 1-19. (Year: 1977).*

(Continued)

*Primary Examiner* — Taylor V Oh

(57) ABSTRACT

This specification generally relates to an improved method for the manufacture of 3-[(1S)-1-imidazo[1,2-a]pyridin-6-ylethyl]-5-(1-methylpyrazol-4-yl)triazolo[4,5-b]pyrazine (I), or pharmaceutically acceptable salts thereof; polymorphic forms thereof, and intermediates useful in the manufacture of such compounds and salts thereof.

13 Claims, 5 Drawing Sheets

(58) Field of Classification Search
USPC .......................................................... 544/350
See application file for complete search history.

(56) References Cited

OTHER PUBLICATIONS

Hong Jia et al; "Discovery of ( S )-1-(1-(Imidazo[1,2- a ]pyridin-6-yl)ethyl)-6-(1-methyl-1 H -Pyrazol-4-yL)-1 H -[1,2,3]triazolo[4,5-b]pyrazine (Volitinib) as a Highly Potent and Selective Mesenchymal—Epithelial Transition Factor (c-Met) Inhibitor in Clinical Development for Treatment of Cancer", Journal of Medicinal Chemistry, vol. 57, No. 18, 2014.

* cited by examiner

METHOD FOR THE MANUFACTURE OF 3-[(1S)-1-IMIDAZO[1,2-A]PYRIDIN-6-YLETHYL]-5-(1-METHYLPYRAZOL-4-YL) TRIAZOLO[4,5-B]PYRAZINE AND POLYMORPHIC FORMS THEREOF

CROSS-REFERENCE TO RELATED APPLICATIONS

This application is a U.S. National Stage application of International Application No. PCT/EP2019/074083, filed on Sep. 10, 2019, which claims the benefit of priority under 35 U.S.C. § 119(a) to CN Application No. PCT/CN2018/104941 filed on Sep. 11, 2018. Each of the above listed applications is hereby incorporated by reference in its entirety for all purposes.

FIELD

This specification relates to an improved method for the manufacture of 3-[(1S)-1-imidazo[1,2-a]pyridin-6-ylethyl]-5-(1-methylpyrazol-4-yl)triazolo[4,5-b]pyrazine, or pharmaceutically acceptable salts thereof; polymorphic forms thereof; and intermediates useful in the manufacture of such compounds and salts thereof.

BACKGROUND

3-[(1S)-1-imidazo[1,2-a]pyridin-6-ylethyl]-5-(1-methylpyrazol-4-yl)triazolo[4,5-b]pyrazine (also known as "Savolitinib", "AZD6094", "HMPL-504", or "volitinib") is a potent and selective small molecule c-Met kinase inhibitor (Jia H. et al., *J. Med. Chem.* 2014; 57; 7577) currently being investigated as a targeted therapy for patients with non-small-cell lung cancer in combination with Osimertinib (Oxnard G R, Ramalingam S S, Ahn M-J, et al., *J Clin Oncol* 33, 2015 (suppl; abstr 2509)) as well as for patients with advanced or metastatic papillary renal cell carcinoma (PRCC).

Savolitinib is described in WO2011079804, the contents of which are incorporated herein by reference. Savolitinib has the following structure:

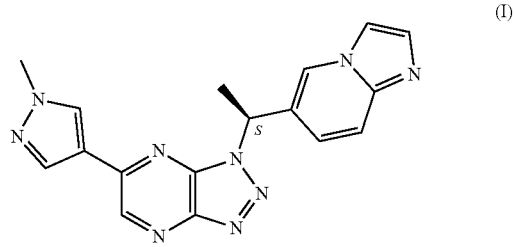

(I)

WO2011079804 describes a 7-step synthesis of Savolitinib starting from 1-imidazo[1,2-a]pyridin-6-ylethanone. The synthetic route is summarised in Scheme 1 below.

Scheme 1

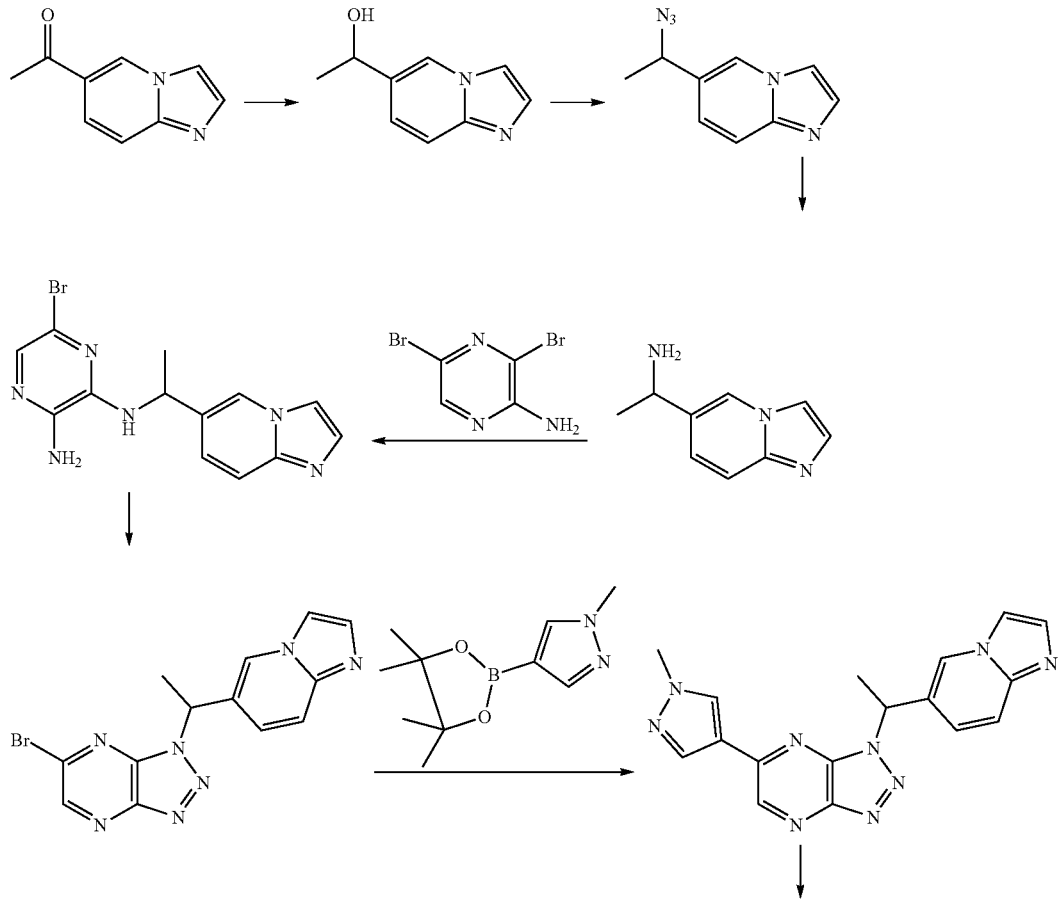

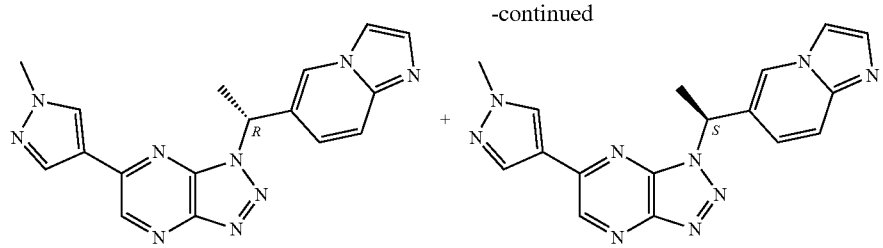

Although providing a reliable method for producing Savolitinib, the synthetic route shown in Scheme 1 has a number of drawbacks, most notably the fact that the final step comprises the chiral resolution of 3-[1-imidazo[1,2-a]pyridin-6-ylethyl]-5-(1-methylpyrrol-3-yl)triazolo[4,5-b]pyrazine into its R and S enantiomers, resulting in the loss of ~50% of the material generated during the entire synthesis. Chiral resolution at this point is inefficient and would generate significant amounts of chemical waste on an industrial scale, which is undesirable. Moreover, this synthetic route does not offer many controlled isolation points for purification (which would be desirable for industrial-scale manufacture) and also requires chromatagraphic purification of 5-bromo-3-(1-imidazo[1,2-a]pyridin-6-ylethyl)triazolo[4,5-b]pyrazine (which would be impractical on an industrial scale).

In summary, whilst the synthetic route shown in Scheme 1 provides a means for the production of Savolitinib, there is a clear need for a robust process that would be more applicable to industrial scale production of this compound.

As a result an improved synthetic process has been developed to Savolitinib which overcomes the drawbacks described above. A summary of this improved process is shown in Scheme 2 below.

Scheme 2

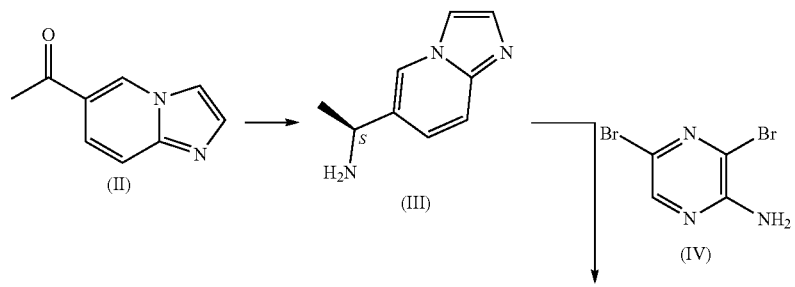

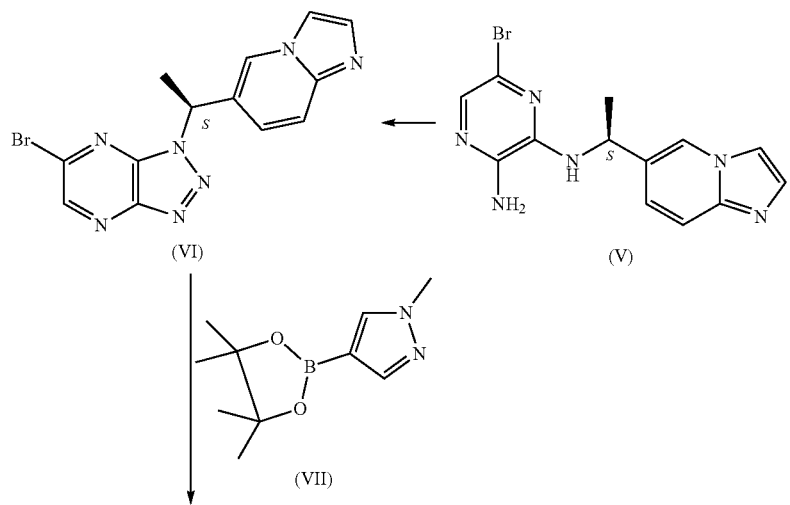

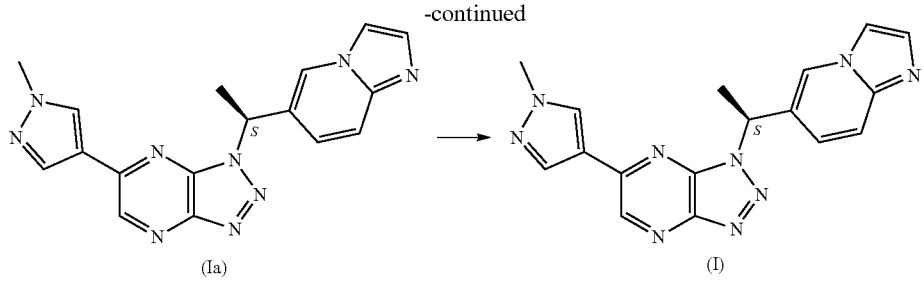

The improved process is not only shorter (5 steps from 1-imidazo[1,2-a]pyridin-6-ylethanone rather than 7 steps) and therefore more efficient than the synthetic route shown in Scheme 1, but also has the advantage of introducing the chiral centre in the first step, producing the chiral intermediate compound (III) which is then carried through the entire synthesis, thus avoiding the need for wasteful chiral resolution of the end product. Moreover, the route enables intermediates (III) and (IV) to be readily isolated and purified, without the need for chromatography.

SUMMARY

Briefly, this specification describes a process for the preparation of Savolinitib (I)

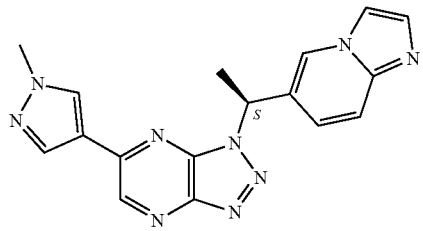

comprising the preparation of (1S)-1-imidazo[1,2-a]pyridin-6-ylethanamine (III),

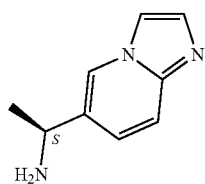

or a pharmaceutically acceptable salt thereof, comprising the steps of (i) enzymatic asymmetric transamination of 1-imidazo[1,2-a]pyridin-6-ylethanone (II),

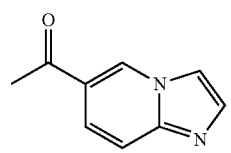

in the presence of an enzyme, an enzyme cofactor and an amine source; and (ii) isolation of (1S)-1-imidazo[1,2-a]pyridin-6-ylethanamine (III), or a pharmaceutically acceptable salt thereof.

This specification also describes a process for the preparation of Savolinitib, comprising the preparation of 5-bromo-N3-[(1S)-1-imidazo[1,2-a]pyridin-6-ylethyl]pyrazine-2,3-diamine (V),

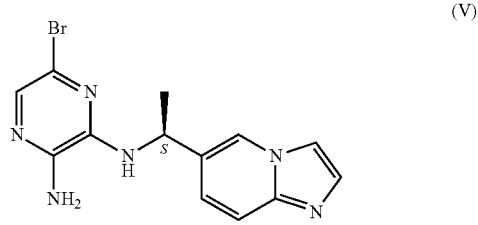

comprising the steps of (iii) neutralising a pharmaceutically acceptable salt of (1S)-1-imidazo[1,2-a]pyridin-6-ylethanamine (III) with a neutralising agent; followed by (iv) the reaction of (1S)-1-imidazo[1,2-a]pyridin-6-ylethanamine (III) with 3,5-dibromopyrazin-2-amine (IV),

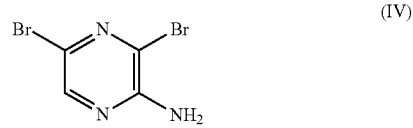

in the presence of an organic base; and isolating 5-bromo-N3-[(1S)-1-imidazo[1,2-a]pyridin-6-ylethyl]pyrazine-2,3-diamine (V).

This specification also describes a process for the preparation of Savolinitib, comprising the preparation of 5-bromo-3-[(1S)-1-imidazo[1,2-a]pyridin-6-ylethyl]triazolo[4,5-b]pyrazine (VI),

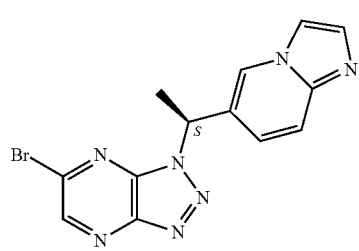

or a pharmaceutically acceptable salt thereof, comprising the steps of (v) cyclisation of 5-bromo-N3-[(1S)-1-imidazo[1,2-a]pyridin-6-ylethyl]pyrazine-2,3-diamine (V), in the presence of sodium nitrite under acidic conditions in an aqueous system; and (vi) isolating 5-bromo-3-[(1S)-1-imidazo[1,2-a]pyridin-6-ylethyl]triazolo[4,5-b]pyrazine (VI) or a pharmaceutically acceptable salt thereof.

This specification also describes a process for the preparation of Savolinitib (I), comprising the steps of (vii) the reaction of 5-bromo-3-[(1S)-1-imidazo[1,2-a]pyridin-6-ylethyl]triazolo[4,5-b]pyrazine (VI), or a pharmaceutically acceptable salt thereof, with 1-methyl-4-(4,4,5,5-tetramethyl-1,3,2-dioxaborolan-2-yl)pyrazole (VII)

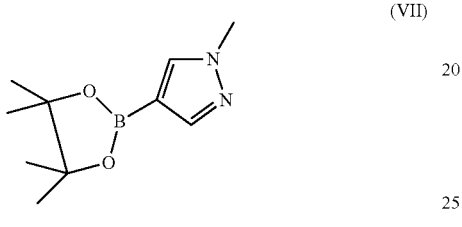

(VII)

in the presence of a palladium catalyst and a suitable base;

(viii) treating crude 3-[(1S)-1-imidazo[1,2-a]pyridin-6-ylethyl]-5-(1-methylpyrazol-4-yl)triazolo[4,5-b]pyrazine with a palladium scavenger;

(ix) isolating crude 3-[(1S)-1-imidazo[1,2-a]pyridin-6-ylethyl]-5-(1-methylpyrazol-4-yl)triazolo[4,5-b]pyrazine following azeotropic distillation; and (x) isolating Savolinitib.

This specification also describes a process for the preparation of Savolinitib (I)

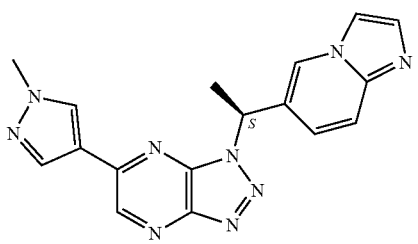

(I)

comprising the preparation of (1S)-1-imidazo[1,2-a]pyridin-6-ylethanamine (III),

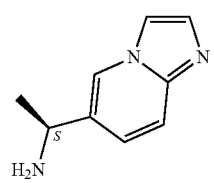

(III)

or a pharmaceutically acceptable salt thereof, comprising the steps of (i) enzymatic asymmetric transamination of 1-imidazo[1,2-a]pyridin-6-ylethanone (II),

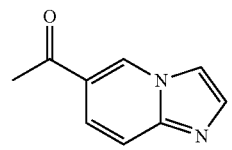

(II)

in the presence of an enzyme, an enzyme cofactor and an amine source; and (ii) isolation of (1S)-1-imidazo[1,2-a]pyridin-6-ylethanamine (III), or a pharmaceutically acceptable salt thereof;

wherein said process additionally comprises the preparation of 5-bromo-N3-[(1S)-1-imidazo[1,2-a]pyridin-6-ylethyl]pyrazine-2,3-diamine (V),

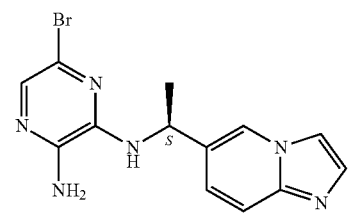

(V)

comprising the steps of (iii) neutralising a pharmaceutically acceptable salt of (1S)-1-imidazo[1,2-a]pyridin-6-ylethanamine (III) with a neutralising agent; followed by (iv) the reaction of (1S)-1-imidazo[1,2-a]pyridin-6-ylethanamine (III) with 3,5-dibromopyrazin-2-amine (IV),

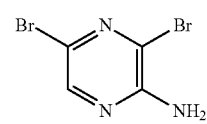

(IV)

in the presence of an organic base; and isolating 5-bromo-N3-[(1S)-1-imidazo[1,2-a]pyridin-6-ylethyl]pyrazine-2,3-diamine (V);

wherein said process additionally comprises the preparation of 5-bromo-3-[(1S)-1-imidazo[1,2-a]pyridin-6-ylethyl]triazolo[4,5-b]pyrazine (VI),

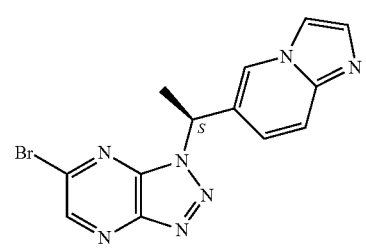

(VI)

or a pharmaceutically acceptable salt thereof, comprising the steps of (v) cyclisation of 5-bromo-N3-[(1S)-1-imidazo[1,2-a]pyridin-6-ylethyl]pyrazine-2,3-diamine (V), in the presence of sodium nitrite under acidic conditions in an aqueous system; and (vi) isolating 5-bromo-3-[(1S)-1-imidazo[1,2-a]pyridin-6-ylethyl]triazolo[4,5-b]pyrazine (VI) or a pharmaceutically acceptable salt thereof;

wherein said process additionally comprises the preparation of Savolinitib (I), comprising the steps of (vii) the reaction of 5-bromo-3-[(1S)-1-imidazo[1,2-a]pyridin-6-ylethyl]triazolo[4,5-b]pyrazine (VI), or a pharmaceutically acceptable salt thereof, with 1-methyl-4-(4,4,5,5-tetramethyl-1,3,2-dioxaborolan-2-yl)pyrazole (VII)

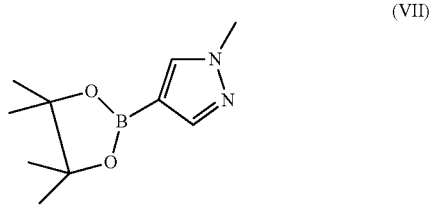

(VII)

in the presence of a palladium catalyst and a suitable base;

(viii) treating crude 3-[(1S)-1-imidazo[1,2-a]pyridin-6-ylethyl]-5-(1-methylpyrazol-4-yl)triazolo[4,5-b]pyrazine with a palladium scavenger;

(ix) isolating crude 3-[(1S)-1-imidazo[1,2-a]pyridin-6-ylethyl]-5-(1-methylpyrazol-4-yl)triazolo[4,5-b]pyrazine following azeotropic distillation; and (x) isolating Savolinitib.

This specification also describes (1S)-1-imidazo[1,2-a]pyridin-6-ylethanamine (III), or a pharmaceutically acceptable salt thereof.

This specification also describes a pharmaceutically acceptable salt of (1S)-1-imidazo[1,2-a]pyridin-6-ylethanamine (III).

This specification also describes a hydrochloride salt of (1S)-1-imidazo[1,2-a]pyridin-6-ylethanamine (III).

This specification also describes a dihydrochloride salt of (1S)-1-imidazo[1,2-a]pyridin-6-ylethanamine (III).

Savolinitib exhibits crystalline properties, and four crystalline forms are described herein: Form I, Form II, Form III and Form IV.

A pharmaceutical composition comprising Savolinitib is also described herein.

A metabolite of Savolinitib, referred to as "HMPL-504-M2", is also described herein.

DETAILED DESCRIPTION

Figure 1:
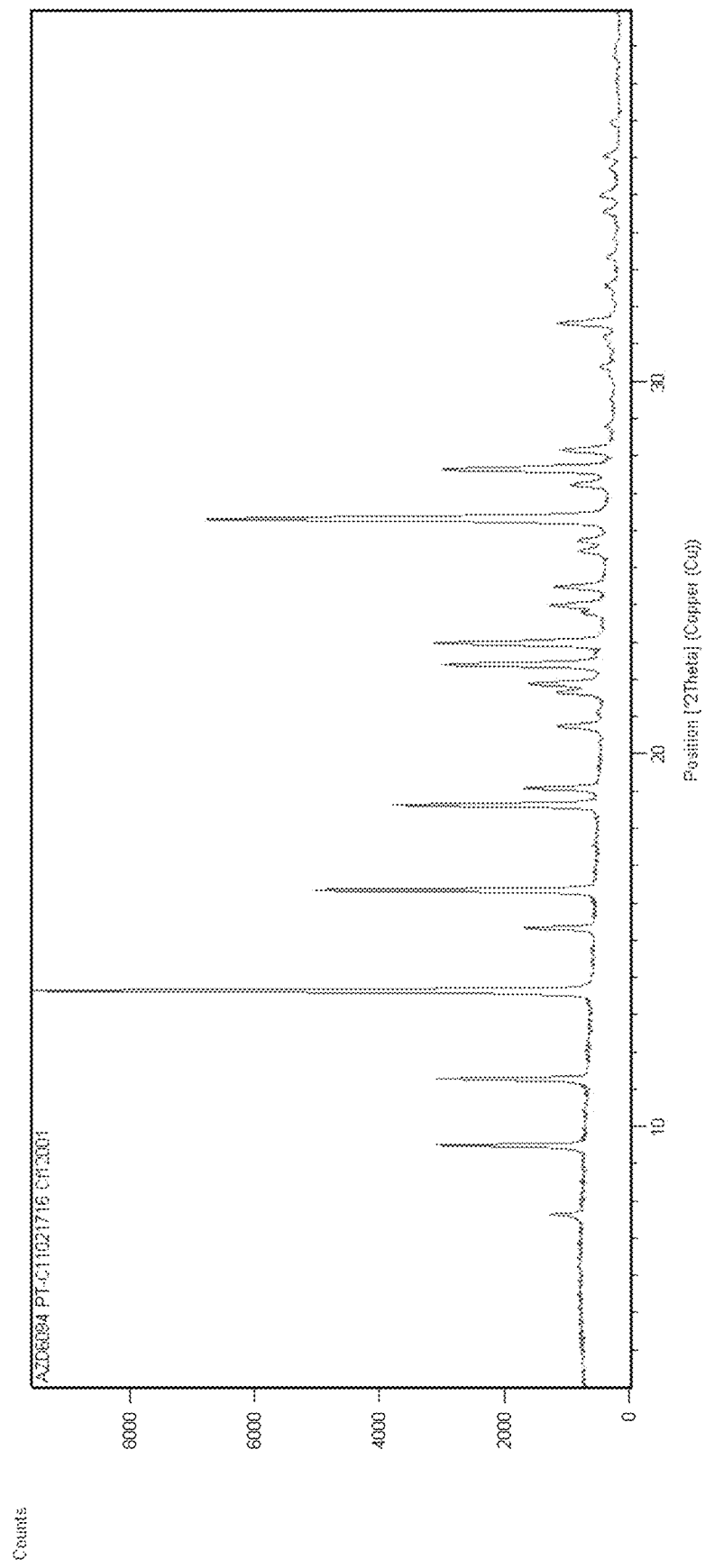
FIG. 1: XRPD pattern of Savolitinib Form I solid.

Many embodiments are detailed throughout the specification and will be apparent to a reader skilled in the art. The invention is not to be interpreted as being limited to any particular embodiment.

In an embodiment there is provided a process for the preparation of Savolinitib (I)

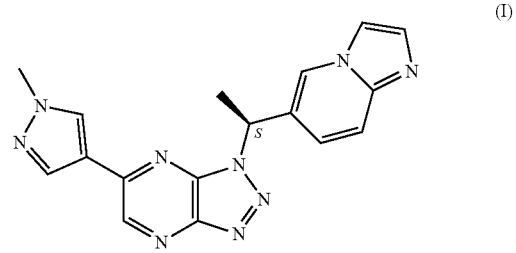

(I)

comprising the preparation of (1S)-1-imidazo[1,2-a]pyridin-6-ylethanamine (III),

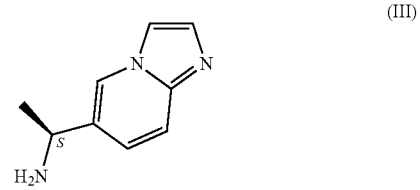

(III)

or a pharmaceutically acceptable salt thereof, comprising the steps of (i) enzymatic asymmetric transamination of 1-imidazo[1,2-a]pyridin-6-ylethanone (II),

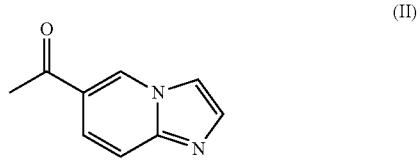

(II)

in the presence of an enzyme, an enzyme cofactor and an amine source; and (ii) isolation of (1S)-1-imidazo[1,2-a]pyridin-6-ylethanamine (III), or a pharmaceutically acceptable salt thereof.

In an embodiment, in step (i), the enzyme is an amine transaminase.

In an embodiment, in step (i), the enzyme is ATA-436.

In an embodiment, in step (i), the enzyme cofactor is pyridoxal phosphate.

In an embodiment, in step (i), the amine source is selected from isopropylamine hydrochloride, S-alphamethylbenzylamine, 1,4-diaminobutane and 1,5-diaminopentane.

In an embodiment, in step (i), the amine source is an alkyl amine.

In an embodiment, in step (i), the amine source is isopropylamine hydrochloride.

In an embodiment, in step (i), a buffer is present.
In an embodiment, in step (i), a pH10 buffer is present.
In an embodiment, in step (i), sodium tetraborate buffer (pH10) is present.

In an embodiment, in step (i), the enzyme is ATA-436, the enzyme cofactor is pyridoxal phosphate and the amine source is isopropylamine hydrochloride.

In an embodiment, in step (i), the enzyme is ATA-436, the enzyme cofactor is pyridoxal phosphate, the amine source is isopropylamine hydrochloride and sodium tetraborate buffer (pH10) is present.

In an embodiment, step (i) is carried out at elevated temperature.

In an embodiment, step (i) is carried out at 44-54° C.

In an embodiment, step (i) is carried out at 49° C.

In an embodiment, in step (ii), (1S)-1-imidazo[1,2-a]pyridin-6-ylethanamine is isolated as a pharmaceutically acceptable salt from an alcoholic solvent.

In an embodiment, in step (ii), (1S)-1-imidazo[1,2-a]pyridin-6-ylethanamine is isolated as a hydrochloride salt from an alcoholic solvent.

In an embodiment, in step (ii), (1S)-1-imidazo[1,2-a]pyridin-6-ylethanamine is isolated as a hydrochloride salt from n-butanol.

In an embodiment, in step (ii), (1S)-1-imidazo[1,2-a]pyridin-6-ylethanamine is isolated as a dihydrochloride salt from n-butanol.

In an embodiment, there is also provided a process for the preparation of Savolinitib, comprising the preparation of 5-bromo-N3-[(1S)-1-imidazo[1,2-a]pyridin-6-ylethyl]pyrazine-2,3-diamine (V),

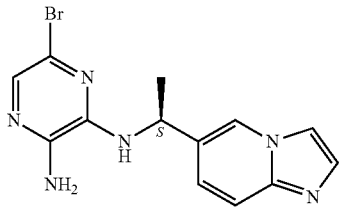

comprising the steps of (iii) neutralising a pharmaceutically acceptable salt of (1S)-1-imidazo[1,2-a]pyridin-6-ylethanamine (III) with a neutralising agent; followed by (iv) the reaction of (1S)-1-imidazo[1,2-a]pyridin-6-ylethanamine (III) with 3,5-dibromopyrazin-2-amine (IV),

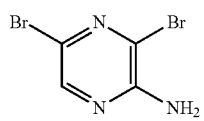

in the presence of an organic base; and isolating 5-bromo-N3-[(1S)-1-imidazo[1,2-a]pyridin-6-ylethyl]pyrazine-2,3-diamine (V).

In an embodiment, in step (iii), (1S)-1-imidazo[1,2-a]pyridin-6-ylethanamine (III) is present as a hydrochloric acid salt.

In an embodiment, in step (iii), (1S)-1-imidazo[1,2-a]pyridin-6-ylethanamine (III) is present as a dihydrochloride salt.

In an embodiment, in step (iii), the neutralising agent is selected from ammonia; a solid-supported base; sodium, potassium, lithium, caesium, magnesium or calcium hydroxides; and sodium, potassium, lithium, caesium, magnesium or calcium alkoxides.

In an embodiment, in step (iii), the neutralising agent is selected from ammonia, Amberlite® IRA-67, sodium hydroxide, sodium methoxide, sodium ethoxide and a sodium isopropoxide.

In an embodiment, step (iii) is carried out in a suitable solvent selected from dichloromethane, methanol, ethanol, isopropanol and N-methyl-2-pyrrolidone.

In an embodiment, step (iii) is carried out in methanol, ethanol, isopropanol or N-methyl-2-pyrrolidone and the neutralising agent is selected from a solid-supported base, sodium hydroxide and a sodium alkoxide.

In an embodiment, step (iii) is carried out in dichloromethane and the neutralising agent is ammonia.

In an embodiment, in step (iv), the organic base is selected from triethylamine, 2,6-di-tert-butylpyridine, 1,5-diazabicyclo(4.3.0)non-5-ene, 1,8-diazabicycloundec-7-ene, dicyclohexylmethylamine and N,N-diisopropylethylamine.

In an embodiment, in step (iv), the organic base is N,N-diisopropylethylamine.

In an embodiment, step (iv) is carried out in a suitable solvent selected from iso-amyl alcohol and N-methyl-2-pyrrolidone.

In an embodiment, step (iv) is carried out in a suitable solvent selected from iso-amyl alcohol and N-methyl-2-pyrrolidone and the organic base is N,N-diisopropylethylamine.

In an embodiment, step (iv) is carried out in N-methyl-2-pyrrolidone and the organic base is N,N-diisopropylethylamine.

In an embodiment, step (iv) is carried out without step (iii) being performed.

In an embodiment, step (iv) is carried out at elevated temperature.

In an embodiment, step (iv) is carried out at 115-125° C.

In an embodiment, step (iv) is carried out at 120° C.

In an embodiment, there is also provided a process for the preparation of Savolinitib, comprising the preparation of 5-bromo-3-[(1S)-1-imidazo[1,2-a]pyridin-6-ylethyl]triazolo[4,5-b]pyrazine (VI),

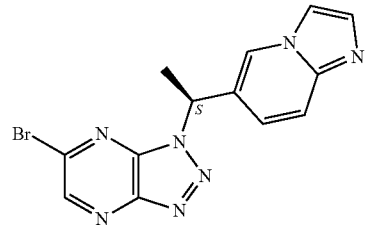

or a pharmaceutically acceptable salt thereof, comprising the steps of (v) cyclisation of 5-bromo-N3-[(1S)-1-imidazo[1,2-a]pyridin-6-ylethyl]pyrazine-2,3-diamine (V), in the presence of sodium nitrite under acidic conditions in an aqueous system; and (vi) isolating 5-bromo-3-[(1S)-1-imidazo[1,2-a]pyridin-6-ylethyl]triazolo[4,5-b]pyrazine (VI), or a pharmaceutically acceptable salt thereof.

In an embodiment, in step (v), the acidic conditions comprise carrying out the reaction in a mixture of toluene and water in the presence of acetic acid or hydrochloric acid.

In an embodiment, in step (v), the acidic conditions comprise carrying out the reaction in a mixture of 2-methyltetrahydrofuran and water in the presence of acetic acid or hydrochloric acid.

In an embodiment, in step (v), the acidic conditions comprise carrying out the reaction in a mixture of acetic acid and water.

In an embodiment, step (v) is carried out at reduced temperature.

In an embodiment, step (v) is carried out at 0-5° C.

In an embodiment, step (i) is carried out at 3-5° C.

In an embodiment, step (v) is carried out at 5° C.

In an embodiment, in step (vi), 5-bromo-3-[(1S)-1-imidazo[1,2-a]pyridin-6-ylethyl]triazolo[4,5-b]pyrazine (VI) is isolated as a pharmaceutically acceptable salt form from an organic solvent.

In an embodiment, in step (vi), 5-bromo-3-[(1S)-1-imidazo[1,2-a]pyridin-6-ylethyl]triazolo[4,5-b]pyrazine (VI) is isolated as a pharmaceutically acceptable salt form from an organic solvent selected from ethyl acetate, methanol, ethanol and isopropanol.

In an embodiment, in step (vi), 5-bromo-3-[(1S)-1-imidazo[1,2-a]pyridin-6-ylethyl]triazolo[4,5-b]pyrazine (VI) is isolated as a hydrochloride salt from ethyl acetate.

In an embodiment, step (vi) is carried out at ambient temperature.

In an embodiment, step (vi) is carried out at less than 25° C.

In an embodiment, step (vi) is carried out at 15-25° C.

In an embodiment, there is also provided a process for the preparation of Savolinitib, comprising the steps of (vii) the reaction of 5-bromo-3-[(1S)-1-imidazo[1,2-a]pyridin-6-ylethyl]triazolo[4,5-b]pyrazine (VI), or a pharmaceutically acceptable salt thereof, (VI)

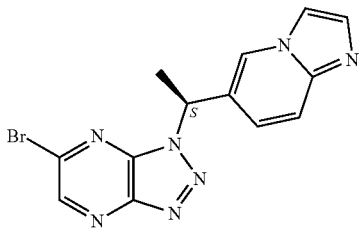

with 1-methyl-4-(4,4,5,5-tetramethyl-1,3,2-dioxaborolan-2-yl)pyrazole (VII)

(VII)

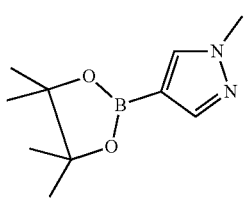

in the presence of a palladium catalyst and a suitable base;
(viii) treating crude 3-[(1S)-1-imidazo[1,2-a]pyridin-6-ylethyl]-5-(1-methylpyrazol-4-yl)triazolo[4,5-b]pyrazine with a palladium scavenger;
(ix) isolating crude 3-[(1S)-1-imidazo[1,2-a]pyridin-6-ylethyl]-5-(1-methylpyrazol-4-yl)triazolo[4,5-b]pyrazine following azeotropic distillation; and
(x) isolating Savolinitib.

In an embodiment, step (vii) comprises the reaction of a pharmaceutically acceptable salt of 5-bromo-3-[(1S)-1-imidazo[1,2-a]pyridin-6-ylethyl]triazolo[4,5-b]pyrazine (VI).

In an embodiment, step (vii) comprises the reaction of a hydrochloride salt of 5-bromo-3-[(1S)-1-imidazo[1,2-a]pyridin-6-ylethyl]triazolo[4,5-b]pyrazine (VI).

In an embodiment, in step (vii), the palladium catalyst is a homogeneous palladium catalyst.

In an embodiment, in step (vii), the palladium catalyst is selected from:

Pd(AmPhos)$_2$Cl$_2$ (Pd-132; dichlorobis[di-tert-butyl(4-dimethylaminophenyl)phosphine]palladium(II));
PdCl$_2$[P(tBu)(Cy)$_2$]$_2$ (Pd-166; bis(tert-butyldicylcohexylphosphine)dichloropalladium(II));
Pd(dppf)Cl$_2$ ([1,1'-bis(diphenylphosphino)ferrocene]dichloropalladium(II));
Na$_2$PdCl$_4$ with DtBPPS (3-(Di-tert-butylphosphonium) propane sulfonate);
Pd(OAc)$_2$ with t-BuPPh$_2$;
Pd(OAc)$_2$ with cataCXium® A (di(1-adamantyl)-n-butylphosphine); and
Pd(OAc)$_2$ with t-Bu$_2$PMe·HBF$_4$.

In an embodiment, in step (vii), the palladium catalyst is selected from Pd(AmPhos)$_2$Cl$_2$ (Pd-132; dichlorobis[di-tert-butyl(4-dimethylaminophenyl)phosphine]palladium(II)); Pd(OAc)$_2$ with t-BuPPh$_2$; and Pd(OAc)$_2$ with cataCXium® A (di(1-adamantyl)-n-butylphosphine).

In an embodiment, in step (vii), the palladium catalyst is Pd(AmPhos)$_2$Cl$_2$ (Pd-132; dichlorobis[di-tert-butyl(4-dimethylaminophenyl)phosphine]palladium(II)).

In an embodiment, in step (vii), the suitable base is an inorganic or organic base.

In an embodiment, in step (vii), the suitable base is selected from K$_3$PO$_4$, K$_2$CO$_3$, KHCO$_3$, DIPEA, Cs$_2$CO$_3$ and Na$_2$CO$_3$.

In an embodiment, in step (vii), the suitable base is selected from DIPEA and K$_2$CO$_3$.

In an embodiment, in step (vii), the suitable base is K$_2$CO$_3$.

In an embodiment, in step (vii), the reaction is carried out in a suitable alcoholic solvent or MeCN.

In an embodiment, in step (vii), the reaction is carried out in a suitable alcoholic solvent selected from a secondary or tertiary alcoholic solvent.

In an embodiment, in step (vii), the reaction is carried out in a suitable alcoholic solvent selected from n-BuOH, t-AmOH, IPA and s-BuOH.

In an embodiment, in step (vii), the reaction is carried out in a suitable alcoholic solvent selected from t-AmOH, IPA and s-BuOH.

In an embodiment, in step (vii), the reaction is carried out in a suitable alcoholic solvent selected from IPA and s-BuOH.

In an embodiment, in step (vii), the reaction is carried out in a suitable alcoholic solvent which is s-BuOH.

In an embodiment, in step (vii), the palladium catalyst is Pd(AmPhos)$_2$Cl$_2$ (Pd-132; dichlorobis[di-tert-butyl(4-dimethylaminophenyl)phosphine]palladium(II)) and the suitable base is K$_2$CO$_3$.

In an embodiment, in step (vii), the reaction is carried out in a suitable alcoholic solvent which is s-BuOH, the palladium catalyst is Pd(AmPhos)$_2$Cl$_2$ (Pd-132; dichlorobis[di-tert-butyl(4-dimethylaminophenyl)phosphine]palladium(II)) and the suitable base is K$_2$CO$_3$.

In an embodiment, step (vii) is carried out at elevated temperature.

In an embodiment, step (vii) is carried out at 50-70° C.

In an embodiment, step (vii) is carried out at 65° C.

In an embodiment, in step (viii), the palladium scavenger is selected from a silica-based scavenger (e.g. QuadraSil® (Johnson Matthey) or Sillabond Thiol (Silicycle)), a polymer resin-based scavenger (e.g. QuadraPure® (Johnson Matthey)), a fibre-based scavenger (e.g. Smopex® (Johnson Matthey)), L-cysteine and activated carbon.

In an embodiment, in step (viii), the palladium scavenger is selected from L-cysteine and activated carbon.

In an embodiment, in step (viii), the palladium scavenger is L-cysteine.

In an embodiment, step (viii) is carried out at elevated temperature.

In an embodiment, step (viii) is carried out at 55-70° C.

In an embodiment, step (viii) is carried out at 65° C.

In an embodiment, in step (ix), azeotropic distillation is carried out in the presence of a solvent selected from ethanol, isopropanol, s-butanol, isoamyl alcohol, methyl ethyl ketone, toluene, cyclohexane, anisole and acetonitrile.

In an embodiment, in step (ix), azeotropic distillation is carried out in the presence of a solvent selected from isopropanol, s-butanol, isoamyl alcohol, anisole and acetonitrile.

In an embodiment, in step (ix), azeotropic distillation is carried out in the presence of anisole.

In an embodiment, step (ix) is carried out at elevated temperature.

In an embodiment, step (ix) is carried out at 65-120° C.

In an embodiment, step (ix) is carried out at 90-120° C.

In an embodiment, in step (x), Savolitinib is isolated from a suitable alcoholic solvent, optionally in the presence of activated carbon.

In an embodiment, in step (x), Savolitinib is isolated from a suitable solvent selected from methanol, ethanol and isopropanol, optionally in the presence of activated carbon.

In an embodiment, in step (x), Savolitinib is isolated from a suitable solvent selected from methanol, ethanol and isopropanol, optionally in the presence of activated carbon and optionally in the presence of water as a co-solvent.

In an embodiment, in step (x), 1%, 2%, 3%, 4% or 5% water is present by volume as a co-solvent.

In an embodiment, in step (x), Savolitinib is isolated from ethanol in the presence of activated carbon.

In an embodiment, in step (x), Savolitinib is isolated from 95:5% v/v ethanol:water in the presence of activated carbon.

In an embodiment, step (x) is carried out at elevated temperature.

In an embodiment, step (x) is carried out at 60-75° C.

In an embodiment, step (x) is carried out at 70° C.

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002. A suitable pharmaceutically acceptable salt of compound (III) or (VI) is, for example, an acid-addition salt. An acid addition salt may be formed by bringing the compound into contact with a suitable inorganic or organic acid under conditions known to the skilled person. An acid addition salt may for example be formed using an inorganic acid selected from hydrochloric acid, hydrobromic acid, sulphuric acid and phosphoric acid. An acid addition salt may also for example be formed using an organic acid selected from trifluoroacetic acid, citric acid, maleic acid, oxalic acid, fumaric acid, tartaric acid, pyruvic acid, methanesulfonic acid, benzenesulfonic acid and para-toluenesulfonic acid. It is to be understood that it may be possible to form salts with acids not specifically listed above, and that as a result the broadest definition of "pharmaceutically acceptable" is not to be limited to only salts formed with the specifically recited acids.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. This specification encompasses all such solvated and unsolvated forms.

Atoms of the compounds and salts described in this specification may exist as their isotopes. This specification encompasses all such compounds where an atom is replaced by one or more of its isotopes (for example a compound where one or more carbon atom is an $^{11}C$ or $^{13}C$ carbon isotope, or where one or more hydrogen atoms is a $^{2}H$ or $^{3}H$ isotope).

Savolitinib exhibits crystalline properties, and four crystalline forms are characterised herein: Form I, Form II, Form III and Form IV. This specification encompasses any crystalline or amorphous form of Savolitinib, or mixture of such forms.

It is generally known that crystalline materials may be characterised using conventional techniques such as X-Ray Powder Diffraction (XRPD). Differential Scanning calorimetry (DSC), Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

The specific crystalline forms described herein provide XRPD patterns substantially the same as the XRPD patterns shown in the Figures, and have the various 2-theta values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Persons skilled in the art of XRPD will further realise that the relative intensity of peaks can also be affected by, for example, grains above 30 μm in size and non-unitary aspect ratios. The skilled person understands that the position of reflections can be affected by the precise height at which the sample sits in the diffractometer, and also the zero calibration of the diffractometer. The surface planarity of the sample may also have a small effect.

As a result of these considerations, the diffraction pattern data presented are not to be taken as absolute values (Jenkins, R & Snyder, R. L. '*Introduction to X-Ray Powder Diffractometry*' John Wiley & Sons 1996; Bunn, C. W. (1948), '*Chemical Crystallography*', Clarendon Press, London; Klug, H. P. & Alexander, L. E. (1974), '*X-Ray Diffraction Procedures*'). It should correspondingly be understood that the crystalline forms embodied herein are not limited to those that provide XRPD patterns that are identical to the XRPD pattern shown in the Figures, and any crystals providing XRPD patterns substantially the same as those shown in the Figures fall within the scope of the corresponding embodiment. A person skilled in the art of XRPD is able to judge the substantial identity of XRPD patterns. Generally, a measurement error of a diffraction angle in an XRPD is approximately plus or minus 0.2° 2-theta, and such degree of a measurement error should be taken into account when considering the X-ray powder diffraction pattern in the Figures and when reading data contained in the Tables included herein.

Figure 5:
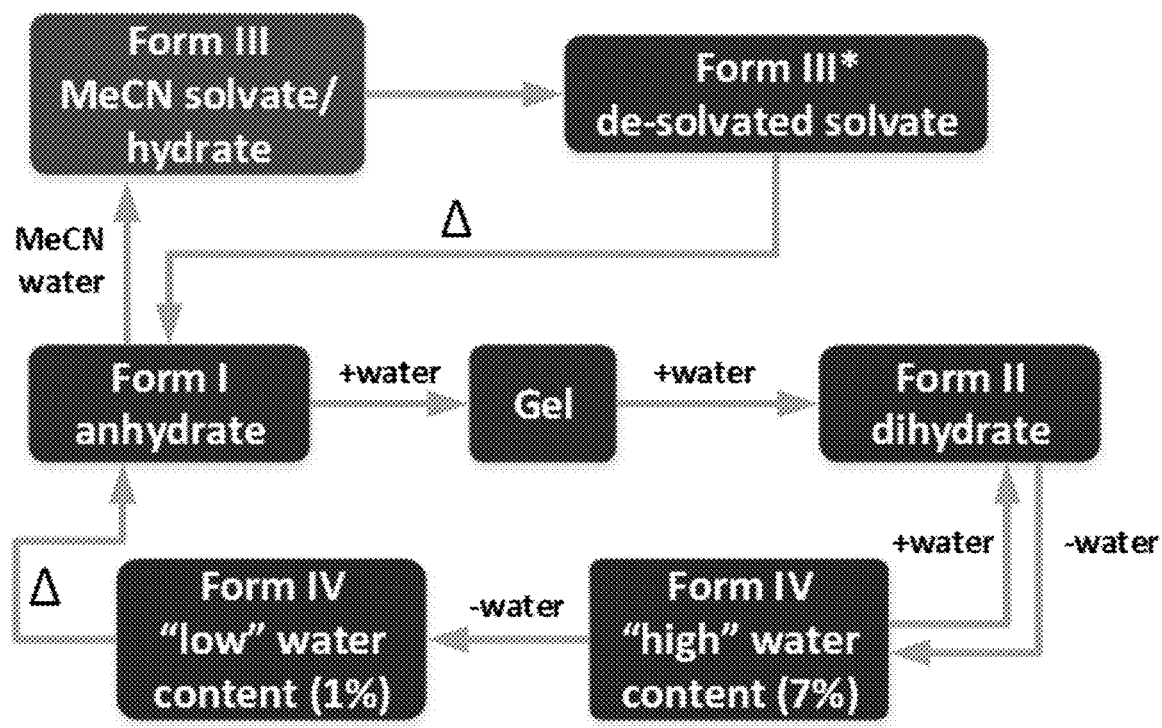
FIG. 5: Interconversion of polymorphic forms of Savolitinib with temperature and water activity ($a_w$)

Savolitinib exhibits crystalline properties, and four crystalline forms are characterised herein. The interconversion of polymorphic forms of Savolitinib with temperature and water activity ($a_w$) is shown in FIG. 5 and Table 1.

TABLE 1

| Water activity ($a_w$) | ≤0.7 | 0.7-0.8 | ≥0.8 |
|---|---|---|---|
| Thermodynamically-stable form | I | IV | II |

In one embodiment there is provided a crystalline form, Form I, of Savolitinib, which has an X-ray powder diffraction pattern comprising specific peaks at about 2-theta=13.6°, 16.3°, 18.6° and 26.3°.

In one embodiment there is provided a crystalline form, Form I, of Savolitinib, which has an X-ray powder diffraction pattern comprising specific peaks at about 2-theta=9.5°, 11.3°, 13.6°, 15.3°, 16.3°, 18.6°, 19.1°, 22.4°, 23.0° and 26.3°.

In one embodiment there is provided a crystalline form, Form I, of Savolitinib, which has an X-ray powder diffraction pattern substantially the same as the X-ray powder diffraction pattern shown in FIG. 1.

In one embodiment there is provided a crystalline form, Form II, of Savolitinib, which has an X-ray powder diffraction pattern comprising specific peaks at about 2-theta=9.1°, 10.3°, 12.4° and 15.8°.

In one embodiment there is provided a crystalline form, Form II, of Savolitinib, which has an X-ray powder diffraction pattern comprising specific peaks at about 2-theta=3.4°, 6.8°, 9.1°, 10.3°, 12.4°, 13.7°, 15.0°, 15.8°, 18.2° and 25.3°.

Figure 2:
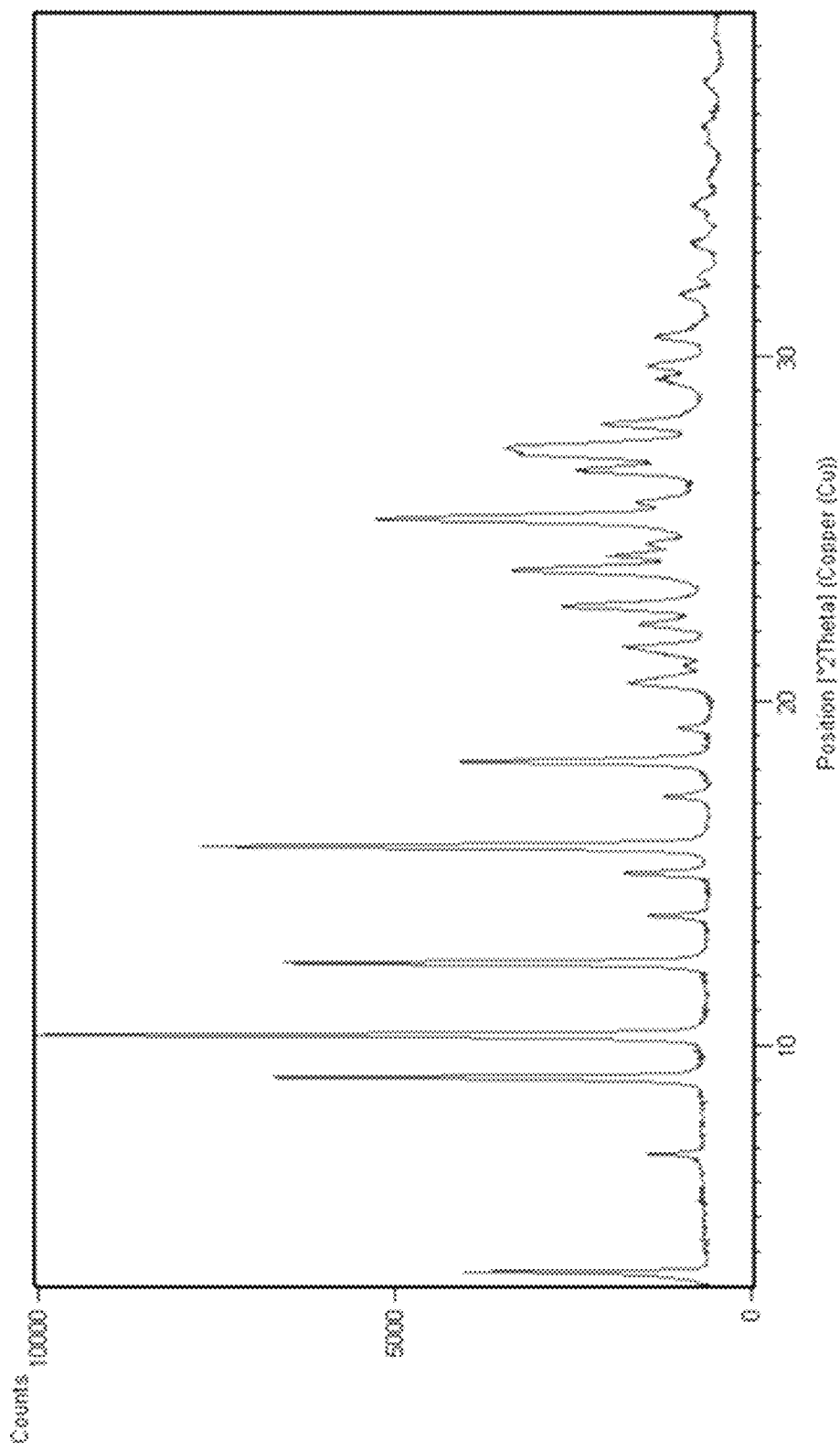
FIG. 2: XRPD pattern of Savolitinib Form II solid.

In one embodiment there is provided a crystalline form, Form II, of Savolitinib, which has an X-ray powder diffraction pattern substantially the same as the X-ray powder diffraction pattern shown in FIG. 2.

In one embodiment there is provided a crystalline form, Form III, of Savolitinib, which has an X-ray powder diffraction pattern comprising specific peaks at about 2-theta=5.3°, 10.6°, 16.0° and 18.5°.

In one embodiment there is provided a crystalline form, Form III, of Savolitinib, which has an X-ray powder diffraction pattern comprising specific peaks at about 2-theta=5.3°, 9.2°, 10.6°, 14.1°, 16.0°, 18.5°, 20.3°, 23.0°, 24.2° and 26.0°.

Figure 3:
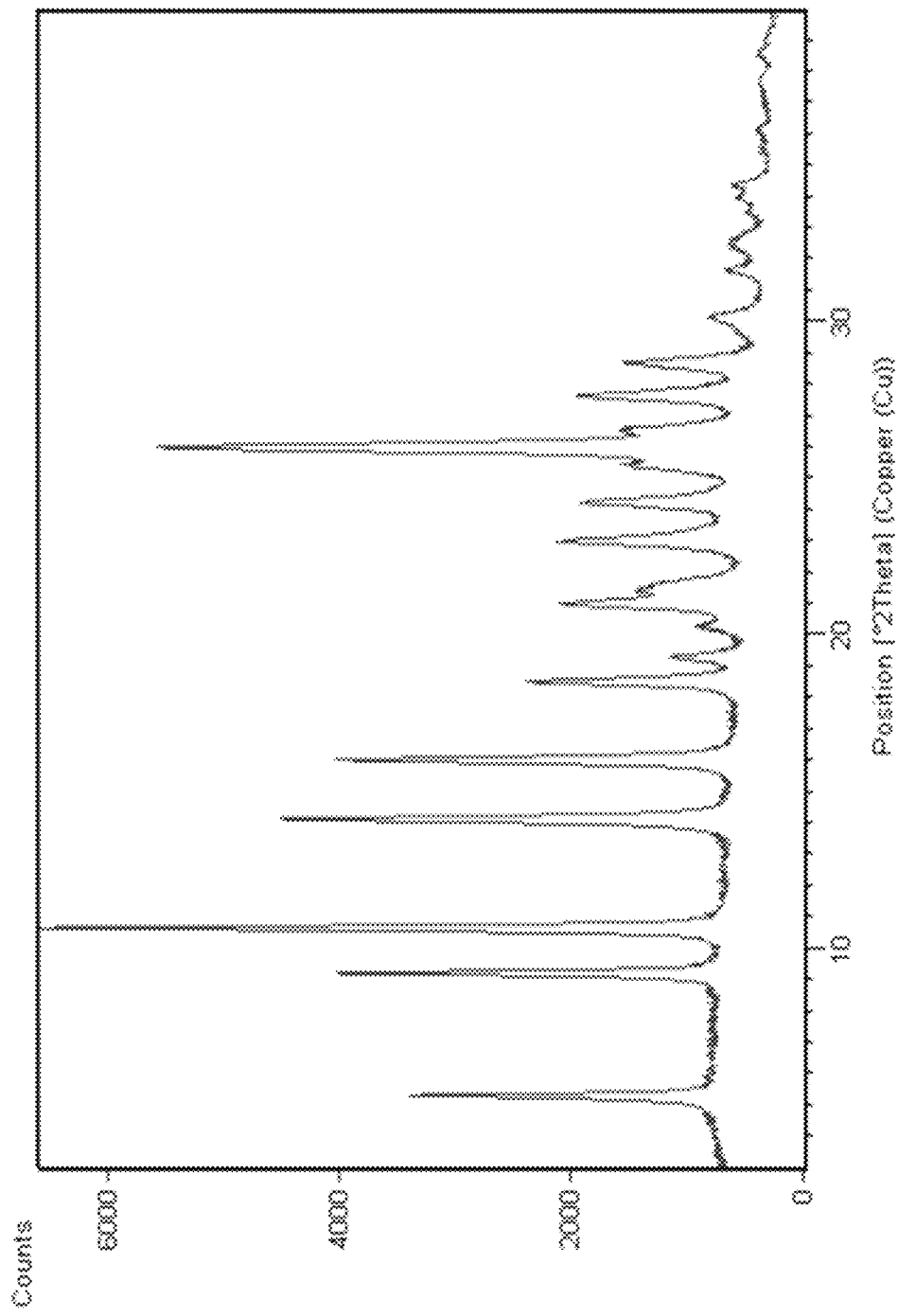
FIG. 3: XRPD pattern of Savolitinib Form III solid.

In one embodiment there is provided a crystalline form, Form III, of Savolitinib, which has an X-ray powder diffraction pattern substantially the same as the X-ray powder diffraction pattern shown in FIG. 3.

In one embodiment there is provided a crystalline form, Form IV, of Savolitinib, which has an X-ray powder diffraction pattern comprising specific peaks at about 2-theta=9.4°, 12.4°, 12.9° and 24.4°.

In one embodiment there is provided a crystalline form, Form IV, of Savolitinib, which has an X-ray powder diffraction pattern comprising specific peaks at about 2-theta=3.5°, 9.4°, 12.4°, 12.9°, 15.6°, 16.4°, 17.9°, 20.9°, 22.7° and 24.4°.

Figure 4:
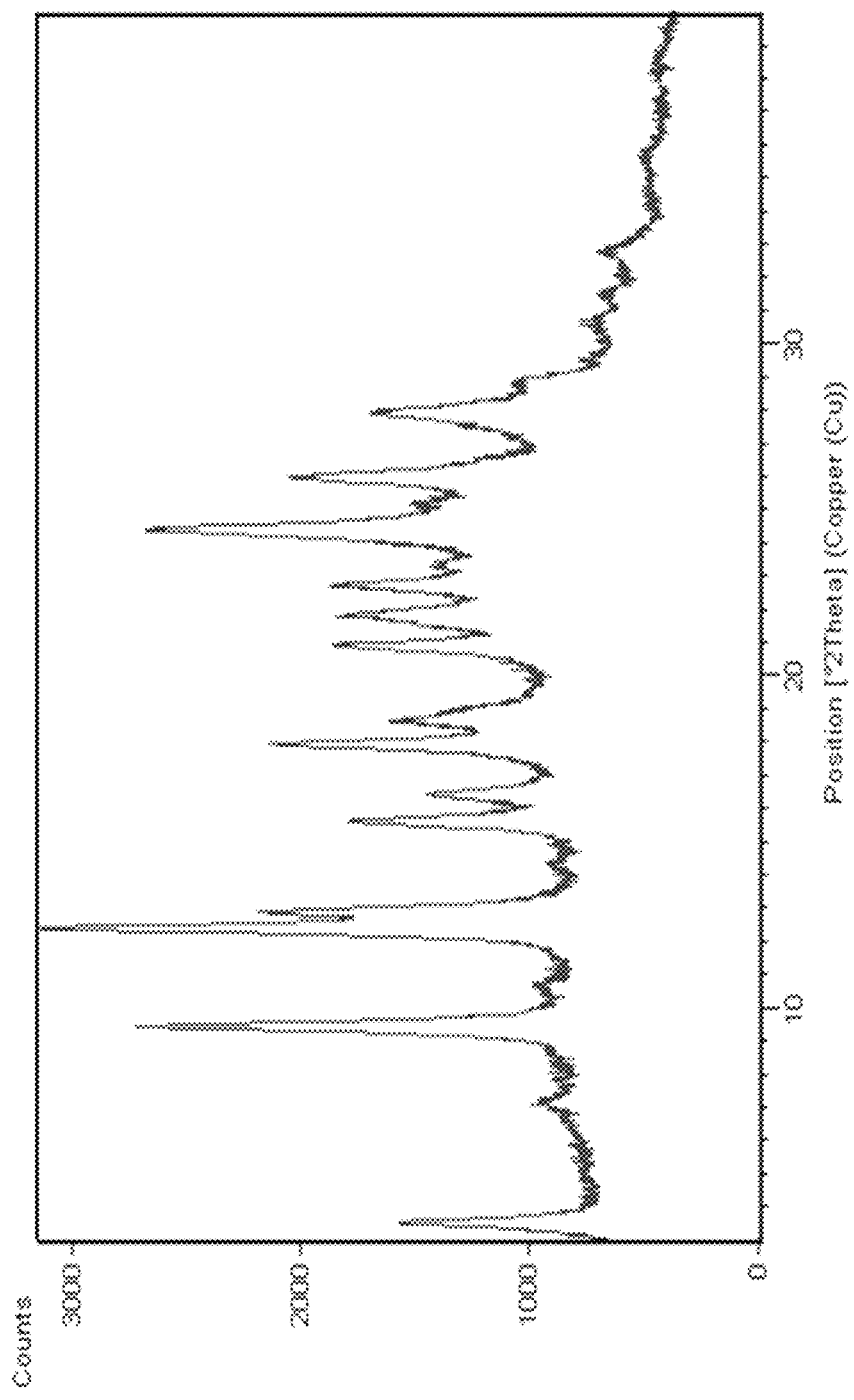
FIG. 4: XRPD pattern of Savolitinib Form IV solid.

In one embodiment there is provided a crystalline form, Form IV, of Savolitinib, which has an X-ray powder diffraction pattern substantially the same as the X-ray powder diffraction pattern shown in FIG. 4.

In the context of 2-theta values of specific peaks within X-ray powder diffraction patterns, the term "about" is used to mean approximately plus or minus 0.2° 2-theta.

As a result of its activity as a c-Met kinase inhibitor, Savolitinib, and crystalline forms thereof, are useful in therapy, for example in the treatment of diseases or medical conditions mediated at least in part by c-Met kinase, including cancer.

Where "cancer" is mentioned, this includes both non-metastatic cancer and also metastatic cancer, such that treating cancer involves treatment of both primary tumours and also tumour metastases.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In an embodiment there is provided a metabolite of Savolitinib, HMPL-504-M2, which has the following structure:

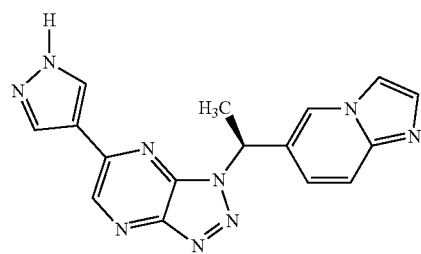

HMPL-504-M2

Savolitinib, prepared by the processes described herein, may be used to provide formulations, such as tablets, for use as medicaments for the treatment of cancer. Suitable formulations and therapeutic uses of the medicaments so prepared are described in WO 2011/079804, the contents of which are hereby incorporated by reference.

In an embodiment, there is provided a pharmaceutical composition comprising Savolitinib in the form of a tablet, optionally in the form of a coated tablet.

EXAMPLES

The various embodiments are illustrated by the following Examples. The invention is not to be interpreted as being limited to the Examples.

Abbreviations Used:
CDI Carbonyldiimidazole
DCM Dichloromethane
DIPEA N,N-diisopropylethyamine
DMSO Dimethyl sulfoxide
ESI Electrospray ionization
HPLC High-performance liquid chromatography
HRMS High-resolution mass spectrometry
iPrOH Isopropanol
mp Melting point
NMP N-Methyl-2-pyrrolidone
NMR Nuclear magnetic resonance spectroscopy Pd-132 Dichlorobis[di-tert-butyl(4-dimethylaminophenyl)phosphine]palladium(II)
PTFE Polytetrafluoroethylene
Q-ToF Quadruple-Time-of-Flight
THF Tetrahydrofuran IUPAC names were generated using Biovia® Draw, version 18.1.

NMR data were collected using a Bruker Ultrashield AV3 400 MHz spectrometer fitted with a BBFO probe and operating with Topspin3.5pl5 software.

HRMS data were collected using a Waters Synapt G2-Si High Definition Mass Spectrometer with ESI ionisation (+ve) and operated with MassLynx V4.1. Sample introduction was via a Waters Aquity H-Class UPLC fitted with a Waters BEH C18 column (100×2.1 mm, 1.7 um).

Melting point data were collected using a Mettler-Toledo Differential Scanning calorimeter fitted with a gold-plated 30 uL sample holder.

Example 1

Preparation of (1S)-1-imidazo[1,2-a]pyridin-6-ylethanamine (III)

Isopropylamine hydrochloride (379.8 g; 3.97 mol), sodium tetraborate decahydrate (31.22 g; 0.08 mol) and pyridoxal phosphate (0.7 g; 0.003 mol) are dissolved in water (2000 ml). The pH is adjusted to pH10 using aqueous NaOH. ATA-436 enzyme (5.94 g) is charged to the reaction vessel. 1-(imidazo[1,2-a]pyridin-6-yl)ethanone (50 g; 0.30 mol), as a solution in DMSO (500 ml), is charged to the reaction vessel. The reaction mixture is heated to 44-54° C. for 72 h.

Upon complete reaction, the mixture is cooled and the pH adjusted to pH 12.0 to 12.5 with aqueous NaOH. Diatomaceous earth (Celite®) (50 g) then nBuOH (625 ml) are charged to the reaction vessel and the contents stirred for approximately 1 h. The mixture is filtered and washed with a mixture of water-DMSO-nBuOH (160 ml-40 ml-300 ml). The filtrate is diluted further with nBuOH (325 ml) and KCl (350 g) is charged to the vessel and the contents agitated for a minimum of 40 min. The organic phase is removed and retained; the aqueous is extracted again with further nBuOH and the organic phase retained. The retained organic phases are combined and concentrated under vacuum with heating (up to 60° C.). The mixture is cooled then filtered. The filtrate is treated with HCl in iPrOH (100 ml; 0.54 mol). The mixture is filtered and washed with nBuOH to provide (1S)-1-imidazo[1,2-a]pyridin-6-ylethanamine dihydrochloride as a solid.

$^1$H NMR (500 MHz, DMSO-$d_6$) δ=9.17 (s, 1H), 9.11 (s, 3H), 8.49 (dd, J=2.1, 0.6 Hz, 1H), 8.29 (dd, J=9.4, 1.6 Hz, 1H), 8.27 (d, J=2.1 Hz, 1H), 8.08 (d, J=9.4 Hz, 1H), 4.63 (s, 1H), 1.64 (d, J=6.9 Hz, 3H); $^{13}$C NMR (DMSO-$d_6$, 126 MHz): δ=138.9, 132.7, 128.6, 128.0, 123.8, 115.7, 112.4, 47.2, 19.4 ppm.

Amine transaminase (ATA) enzymes are available from Codexis, Inc. (https://www.codexis-estore.com; 200 Penobscot Drive, Redwood City, CA 94063, United States).

1-(imidazo[1,2-a]pyridin-6-yl)ethanone (II) may be prepared according to the methods described in *J. Med. Chem.* 2014, 57, 7577 (S13-S14) and WO2011079804, or as below:

1-(imidazo[1,2-a]pyridin-6-yl) ethanone

N-methoxy-N-methyl-imidazo[1,2-a]pyridine-6-carboxamide (200 Kg) was added to a reaction vessel along with THF (370 Kg). The reaction mixture was cooled to 5-15° C. A solution of 3M methylmagnesium bromide in methyl-THF (780 Kg) was added dropwise to the reaction mixture, whilst ensuring the temperature did not exceed 20° C. The resulting reaction mixture was stirred for 8 hours at 10-20° C. The reaction mixture was then quenched with water (10 volumes), whilst ensuring the temperature did not exceed 30° C., and then stirred for a further 2-3 hours at 10-20° C. The pH of the reaction mixture was adjusted to pH 7-8 using 10% $H_2SO_4$ and then the mixture stirred for a further 3-5 hours at 10-20° C. The reaction mixture was concentrated to 19-20 times its original volume (temperature<30° C.) and then stirred for 1-2 hours at 10-20° C. before being filtered. The filter cake was washed with water and then dried under vacuum (50-60° C. for 36-48 hours) to yield the product.

N-methoxy-N-methyl-imidazo[1,2-a]pyridine-6-carboxamide

Imidazo[1,2-a]pyridine-6-carboxylic acid (155 Kg) was added to a reaction vessel along with acetonitrile (1100 Kg). CDI (263 Kg) was then added and the mixture stirred for 16 hours at 10-20° C. N-methoxymethanamine hydrochloride (121 Kg) was then added and the reaction mixture stirred for 24 hours at 5-12° C. The reaction mixture was quenched with water (2 volumes) whilst ensuring the temperature did not exceed 20° C. The quenched mixture was then concentrated to 4-5 times its original volume and extracted with DCM (2 volumes; 5 times). The organic layer was washed with water (2 volumes; 2 times) before being concentrated to 1.5-2.5 times its original volume. The residue was then diluted with THF (2 volumes) to yield a solution of the product.

Imidazo[1,2-a]pyridine-6-carboxylic acid 6-aminopyridine-3-carboxylic acid (183 Kg) was added to a reaction vessel along with water (366 Kg) and the temperature of the mixture adjusted to 75-80° C. 2-chloroacetaldehyde (40% aqueous solution; 320 Kg) was added dropwise and the mixture stirred at 75-80° C. for 4 hours. The temperature was then adjusted to 45-55° C. and acetone (8 volumes) added dropwise. The mixture was then stirred at 45-55° C. for 2-3 ours before being cooled to −10° C. and stirred at this temperature for 18-24 hours. The reaction mixture was then filtered and the filter cake rinsed with acetone and then dried under vacuum (55-60° C.) to yield the product.

Example 2

Preparation of 5-bromo-N3-[(1S)-1-imidazo[1,2-a]pyridin-6-ylethyl]pyrazine-2,3-diamine (V)

(1S)-1-imidazo[1,2-a]pyridin-6-ylethanamine dihydrochloride (70 g, 0.281 mol) is suspended in DCM (263 mL), cooled to 10° C., and treated with a solution of aqueous 28% $NH_3$ (76 mL) and water (259 mL). The reaction stirred at 20° C. for 30 min to 1 h. The mixture is then allowed to settle, the organic phase is separated and retained, and the aqueous phase is extracted 4 times with a mixture of DCM-iPrOH (441 ml-41 mL) The resulting organic phases are combined and concentrated under vacuum to yield (1S)-1-imidazo[1,2-a]pyridin-6-ylethanamine.

NMP (89 mL), 3,5-dibromopyrazin-2-amine (91.02 g, 0.3599 mol) and DIPEA (96.1 mL, 0.551 mol) are added to the (1S)-1-imidazo[1,2-a]pyridin-6-ylethanamine, and the mixture is heated at 120° C. for 20-48 h. Upon reaction completion, the mixture is cooled to 80° C., diluted with further NMP (89 mL) and the temperature maintained at 80° C. The mixture is then charged into water (888 mL, 20° C.). The resulting slurry is stirred at 20° C. for 2 h and then filtered, and the filter cake washed with water (89 mL). The filter cake is pulled dry under vacuum for 30 min. The filter cake is then treated with methanol (222 mL) and stirred at 65-70° C. for 1 h. The mixture is held at 20° C. for 1 h, filtered, and the filter cake washed 3 times with further methanol (44.4 mL). The filter cake is dried to constant weight under vacuum to yield 5-bromo-N3-[(1S)-1-imidazo[1,2-a]pyridin-6-ylethyl]pyrazine-2,3-diamine as a solid.

mp 192.8-206.1° C.; $^1$H NMR (400 MHZ, DMSO-$d_6$) δ=8.49 (s, 1H), 7.95 (s, 1H), 7.56 (m, 2H), 7.28 (dd, J=1.2, 9.3 Hz, 1H), 7.21 (s, 1H), 6.89 (br d, J=6.9 Hz, 1H), 6.31 (s, 2H), 5.11 (quin, J=6.8 Hz, 1H), 1.55 (d, J=6.9 Hz, 3H); $^{13}$C NMR (DMSO-$d_6$, 101 MHz): δ=143.9, 143.1, 141.8, 133.2, 128.3, 127.9, 124.2, 123.7, 121.6, 116.6, 113.2, 47.4, 21.7 ppm; HRMS (ESI/Q-ToF) m/z: [M+H]$^+$ Calculated for $C_{17}H_{20}ON_5$ 333.0458; Found 333.0459.

3,5-dibromopyrazin-2-amine (IV) is commercially available.

Example 3

Preparation of 5-bromo-3-[(1S)-1-imidazo[1,2-a]pyridin-6-ylethyl]triazolo[4,5-b]pyrazine (VI)

A solution of sodium nitrite (11.3 g, 163.3 mmol) in water (90 mL) is prepared and added dropwise to a stirring solution of 5-bromo-N3-[(1S)-1-imidazo[1,2-a]pyridin-6-ylethyl]pyrazine-2,3-diamine (45.0 g, 126 mmol) in water (135 mL) and acetic acid (86.4 mL) at approximately 5° C. The reaction was stirred at approximately 5° C. for a minimum of 4 h.

Upon complete reaction, the solution is charged with 2-methyltetrahydrofuran (450.0 mL) and the mixture stirred for 30 min. The mixture is left to settle for 30 min and then the organic phase is extracted and retained. The aqueous extract is then charged with 2-methyltetrahydrofuran (225.0 mL) and the mixture is stirred for 30 min. The mixture is left to settle for 30 min and then the organic phase is extracted and retained. The combined organic phase extracts are stirred with diatomaceous earth (Celite®) (9 g) and 20% wt/wt aqueous sodium chloride (225.0 ml). The Celite® is removed by filtration and the filtrates are phase separated, and the organic phase extract is retained. The aqueous phase extract is charged with 2-methyltetrahydrofuran (180.0 mL) and the mixture is stirred for 30 min, and then the organic phase is extracted and retained. The combined organic phase extracts are treated with 1.0M HCl in ethyl acetate (151.0 mL), keeping the temperature below 25° C. The mixture is stirred for a minimum of 4 h. The resulting slurry is filtered, washing with 2-methyltetrahydrofuran (360.0 mL). The filter cake is dried under vacuum at ambient temperature to a constant weight to give 5-bromo-3-[(1S)-1-imidazo[1,2-a]pyridin-6-ylethyl]triazolo[4,5-b]pyrazine hydrochloride as a solid.

mp 163.9-169.6° C.; $^1$H NMR (400 MHZ, DMSO-$d_6$) δ=9.07-9.04 (m, 1H), 9.03 (s, 1H), 8.34 (d, J=2.0 Hz, 1H), 8.21 (d, J=2.0 Hz, 1H), 8.07 (dd, J=1.6, 9.5 Hz, 1H), 8.02 (d, J=9.4 Hz, 1H), 6.64 (q, J=7.0 Hz, 1H), 2.17 (d, J=7.1 Hz, 3H); $^{13}$C NMR (DMSO-$d_6$, 101 MHZ): δ=147.6, 146.0, 140.7, 139.0, 138.0, 132.4, 129.0, 127.2, 123.7, 115.8, 112.8, 55.0, 20.0 ppm; HRMS (ESI/Q-ToF) m/z: [M+H–$N_2$]$^+$ Calculated for $C_{13}H_{13}BrN_5$ 318.0349; Found 318.0200.

Example 4

Preparation of 1-methyl-4-(4,4,5,5-tetramethyl-1,3,2-dioxaborolan-2-yl)pyrazole (VII)

A mixture of 4-Bromo-1-methyl-1H-pyrazole (108 kg, 670.8 mol), tri-isopropyl borate (158 kg, 838.5 mol), THF (807 L) and toluene (630 L) are stirred under nitrogen. The mixture is stirred and cooled to 75 to −65° C. before 2.5M n-butyl lithium in hexane (411 L, 279 kg, 1026.3 mol) is added. After stirring for 1 to 1.5 h, the mixture is treated with pinacol (113 kg, 959.2 mol) and allowed to warm to ambient. The reaction is stirred at room temperature for 1-2 h.

Upon completion of the reaction, 15% aqueous acetic acid (about 432 kg) is added slowly at 10 to 20° C. to adjust the mixture to pH 7-8. The mixture is then stirred for 15 to 30 min and then allowed to settle for 15 to 30 min. The aqueous phase is separated and the organic phase is retained. The aqueous phase extract is treated with 2-methyltetrahydrofuran (1026 kg) and the mixture is stirred for 15 to 30 min and then allowed to settle for 15 to 30 min. The organic phase is extracted, combined with the reaction organic phase and concentrated under vacuum to 3-4 volumes, maintaining the temperature at ≤50° C. The mixture is cooled to 20-30° C. and filtered, washing with 2-methyltetrahydrofuran (126 kg). The filtrate is then treated with heptane (1026 kg) and the resulting mixture is concentrated under vacuum to 3-4 volumes, maintaining the temperature at ≤50° C. The concentrated mixture is cooled to 20-30° C. and then treated with heptane (1026 kg). The resulting mixture is concentrated under vacuum to 2-3 volumes, maintaining the temperature at ≤50° C. The resulting concentrated mixture is cooled to 15 to −5° C., and stirred at 15 to −5° C. for 1 to 2 h. The mixture is then filtered, and the filter cake is washed with pre-cooled (−15 to −5° C.) heptane (216 kg). The filtered cake is dried at 35-45° C. under vacuum, to give 1-methyl-4-(4,4,5,5-tetramethyl-1,3,2-dioxaborolan-2-yl)pyrazole.

$^1$H NMR (500 MHz, DMSO-$d_6$) δ=7.88 (s, 1H), 7.53-7.60 (m, 1H), 3.83 (s, 3H), 1.23 (s, 12H); $^{13}$C NMR (DMSO-$d_6$, 126 MHZ): δ=144.5, 137.5, 105.8, 82.8, 38.1, 24.6 ppm.

4-Bromo-1-methyl-1H-pyrazole is commercially available.

Example 5

Preparation of crude 3-[(1S)-1-imidazo[1,2-a]pyridin-6-ylethyl]-5-(1-methylpyrazol-4-yl)triazolo[4,5-b]pyrazine (1a)

Under positive nitrogen pressure, a mixture of 5-bromo-3-[(1S)-1-imidazo[1,2-a]pyridin-6-ylethyl]triazolo[4,5-b]pyrazine hydrochloride (35 g, 85.5 mmol), 1-methyl-4-(4,4,5,5-tetramethyl-1,3,2-dioxaborolan-2-yl)-1H-pyrazole (23.8 g, 111 mmol), potassium carbonate (29.6 g, 214 mmol), water (263 mL) and butan-2-ol (438 mL) is stirred for 5 min. The mixture is then heated to 30° C. and treated with Pd-132 catalyst (0.61 g, 0.86 mmol). The mixture is then stirred at 65° C. for 2 h.

Upon completion, the resulting biphasic mixture is adjusted to 55° C. and stirred with L-cysteine (7.77 g, 64.1 mmol), then stirred at 65° C. for 6 h. The stirring is then stopped and the mixture is allowed to settle. The aqueous phase is removed and the organic phase is treated with 14% w/w sodium chloride solution (35.0 mL). The resulting mixture is stirred at 65° C. for 30 min, then stirring is stopped and the mixture is allowed to settle. The aqueous phase is removed and the organic phase is retained.

The organic phase is diluted with anisole (140 mL) and stirred at 65° C. The mixture is filtered. The filtrate is treated with water (35 mL) and the resulting mixture is stirred at 65° C. for 30 min. The stirring is then stopped and the mixture is allowed to settle. The aqueous phase is removed and the organic phase is dried azeotropically via distillation at atmospheric pressure. The mixture is concentrated to approximately 8 relative volumes. The temperature is adjusted to 90° C. and further anisole (278 mL) is added. The mixture is then stirred and azeotropically dried by distillation, with the mixture concentrated to approximately 10 relative volumes. The mixture is adjusted to 85° C. and 3-[(1S)-1-imidazo[1,2-a]pyridin-6-ylethyl]-5-(1-methylpyrazol-4-yl)triazolo[4,5-b]pyrazine seed crystals (0.07 g, 0.2 mmol) are added. The mixture is stirred for 1 h, then cooled to 0° C., with stirring, over 8 h. The mixture is stirred for a further 2 h at 0° C. before the mixture is filtered. The filter cake is washed twice with pre-cooled (<5° C.) buan-2-ol (35 mL) and then dried under vacuum at 40° C. to give crude 3-[(1S)-1-imidazo[1,2-a]pyridin-6-ylethyl]-5-(1-methylpyrazol-4-yl)triazolo[4,5-b]pyrazine as a beige/red solid.

Example 6

Preparation of 3-[(1S)-1-imidazo[1,2-a]pyridin-6-ylethyl]-5-(1-methylpyrazol-4-yl)triazolo[4,5-b]pyrazine (I)

A mixture crude 3-[(1S)-1-imidazo[1,2-a]pyridin-6-ylethyl]-5-(1-methylpyrazol-4-yl)triazolo[4,5-b]pyrazine (108 g, 0.31 mol), activated carbon (10.7 g), ethanol (2850 mL) and water (150 mL) is stirred at at least 76° C. for 2 h. The activated carbon is removed via filtration at >70° C., washing with ethanol (229 mL) and water (11.8 mL).

The resulting filtrate is then stirred at 75° C. to achieve compete dissolution of the solid. The resulting solution is cooled to 62° C. at a rate of 0.1° C./min. The solution is charged with 3-[(1S)-1-imidazo[1,2-a]pyridin-6-ylethyl]-5-(1-methylpyrazol-4-yl)triazolo[4,5-b]pyrazine seed (5.36 g, 0.02 mol).

An IKA® type[†] wet mill (or mechanically comparable device) is configured with the 6F+2P arrangement and set to a tip speed of 23 m/s with the wet mill jacket heated to ensure the output of the wet mill is 65° C. prior to the start of milling.

The resulting mixture is passed through the wet mill for 75-80 theoretical passes and then stirred at 62° C. for 6 h. The mixture is then cooled to 0° C. at a rate of 0.1° C./min and then stirred for 2 h at 0° C. The mixture is then heated to 65° C. at a rate of 0.35° C./min, and then stirred for 30 min at 65° C. The mixture is then cooled to 0° C. at a rate of 0.14° C./min, and then stirred for 3 h at 0° C. The mixture is then heated to 65° C. at a rate of 0.35° C./min and then stirred for 30 min at 65° C. The mixture is then cooled to 0° C. at a rate of 0.14° C./min and then stirred for 3 h at 0° C.

The wet mill is configured with the 6F+2P arrangement and set to a tip speed of 20.5 m/s with the wet mill jacket cooling engaged to cool the mill to 0° C. prior to the start of milling.

The mixture is passed through the wet mill for 80-90 theoretical passes at 0° C. The mixture is then heated to 65° C. at a rate of 0.35° C./min, and then stirred for 30 min at 65° C. The mixture is then cooled to 0° C. at a rate of 0.14° C./min, and then stirred for 3 h at 0° C. The mixture is then heated to 65° C. at a rate of 0.35° C./min, and then stirred for 30 min at 65° C. The mixture is then cooled to 0° C. at a rate of 0.14° C./min, and then stirred for 3-5 h at 0° C.

The mixture is then filtered, and the wet cake washed with pre-cooled (<5° C.) ethanol (214 mL). The cake is dried to constant weight in a vacuum oven at 45-55° C. to give 3-[(1S)-1-imidazo[1,2-a]pyridin-6-ylethyl]-5-(1-methylpyrazol-4-yl)triazolo[4,5-b]pyrazine as an off-white coloured solid. The material is de-lumped through a 2 mm screen.

mp 205.9-208.8° C.; $^1$H NMR (400 MHz, DMSO-$d_6$) δ=9.19 (s, 1H), 8.83 (s, 1H), 8.64 (s, 1H), 8.31 (s, 1H), 8.01 (s, 1H), 7.62-7.55 (m, 2H), 7.42 (dd, J=1.7, 9.4 Hz, 1H), 6.45 (q, J=7.1 Hz, 1H), 3.98 (s, 3H), 2.22 (d, J=7.1 Hz, 3H); $^{13}$C NMR (DMSO-$d_6$, 101 MHz): δ=147.9, 147.2, 143.9, 141.9, 138.5, 137.4, 133.7, 131.6, 125.4, 124.3, 123.9, 119.4, 117.1, 113.8, 55.5, 40.1, 39.1, 19.6 ppm; HRMS (ESI/Q-ToF) m/z: [M+H−$N_2$]$^+$ Calculated for $C_{17}H_{16}N_7$ 318.1462; Found 318.1486.

[†]IKA® England Limited, Pure Offices, Suite 1 Fountain House, John Smith Drive, Oxford Business Park, Oxford, OX4 2JY, ENGLAND Characterisation of Crystalline Forms of Savolitinib Savolitinib exhibits crystalline properties, and four crystalline forms (Forms I-IV) are characterised herein.

Form I material was generated according to the methods described in Example 6 above. Forms II-IV were generated as described below, utilising one or more of the following techniques:

Temperature Cycling

To a suspension of 3-[(1S)-1-imidazo[1,2-a]pyridin-6-ylethyl]-5-(1-methylpyrazol-4-yl)triazolo[4,5-b]pyrazine, eight to twelve cycles of the following temperature program were performed using the Clarity crystallisation station (available from www.electrothermal.com):

Heat from 20° C. to 60-80° C. at 1° C./min
Cool to 20° C. at 1° C./min
Stirrer speed-600 rpm Sonication Sufficient 3-[(1S)-1-imidazo[1,2-a]pyridin-6-ylethyl]-5-(1-methylpyrazol-4-yl)triazolo[4,5-b]pyrazine was added to a selected solvent until excess undissolved solids remained. The slurry was then shaken at ambient temperature overnight and filtered through a 0.2 μm PTFE syringe filter. The filtrate was sonicated at 70% intensity using a Cole-Parmer® 130 W ultrasonic processor (available from www.coleparmer.com) using a pulsed program. In cases where no solids precipitated at ambient temperature, the sample was stored at 4° C. for 18 hours. If there was still no precipitate present, the samples were exposed to slow or fast evaporation techniques depending on the boiling point of the solvent used. When using solvents in which the compound displayed inadequate solubility, slurries or pastes were prepared and sonicated using the same method. All recovered solids were analysed using XRPD.

Crash Precipitation Solutions of 3-[(1S)-1-imidazo[1,2-a]pyridin-6-ylethyl]-5-(1-methylpyrazol-4-yl)triazolo[4,5-b]pyrazine were prepared in various solvents and filtered through a 0.2 μm PTFE filter. Aliquots (400 μL to 1000 μL) of the prepared saturated solutions were added into the appropriate anti-solvent (10 volumes) at ambient temperature. Experiments that crashed out solids immediately were filtered as soon as possible and air-dried before analysis. Experiments which did not precipitate were stored at 4° C. for 2 days.

Slurry Experiments

Sufficient 3-[(1S)-1-imidazo[1,2-a]pyridin-6-ylethyl]-5-(1-methylpyrazol-4-yl)triazolo[4,5-b]pyrazine was added to a given solvent until undissolved solids remained at the desired temperature (5 or 50° C.). The vial was sealed and the slurry was maintained at the selected temperature and agitated by magnetic stirring for 6-9 days. Solids were isolated by filtration/centrifugation and air dried prior to analysis by XRPD.

Slow Cooling

Sufficient 3-[(1S)-1-imidazo[1,2-a]pyridin-6-ylethyl]-5-(1-methylpyrazol-4-yl)triazolo[4,5-b]pyrazine was added to a given solvent until undissolved solids remained at 3° C. under the boiling point of the solvent. The warm suspension was filtered through a pre-heated (50° C.) 0.2 μm PTFE syringe filter into a pre-heated (boiling point of solvent −3° C.) HPLC vial in the Clarity station (available from www-.electrothermal.com). The solutions were cooled at 0.1° C./min to a final temperature of −10° C. Experiments that precipitated solids were filtered immediately and air dried before analysis.

Fast Evaporation

A solution of 3-[(1S)-1-imidazo[1,2-a]pyridin-6-ylethyl]-5-(1-methylpyrazol-4-yl)triazolo[4,5-b]pyrazine was prepared in each solvent and filtered through a 0.2 μm PTFE filter. The filtered solution was evaporated in a fume hood at ambient temperature in a vial capped under a stream of nitrogen. The resulting solids were analysed by XRPD.

Form II material was observed from experiments employing temperature cycling and sonication methods using tetrahydrofuran:water (67:33% v/v) and crash precipitation from 1,2 propanediol using water as antisolvent. In all cases, very limited drying of recovered solid was necessary to avoid conversion to Form IV.

Form III material was generated from experimental techniques of temperature cycling, high and low temperature slurrying, slow cooling and sonication using acetonitrile:water (87:13% v/v) solvent mixture.

Form IV material was recovered from slow evaporation and both high and low temperature slurrying experiments in tetrahydrofuran:water (67:33% v/v); temperature cycling and sonication in presence of water; or freeze drying or fast evaporation from dioxane:water (18% v/v).

XRPD traces were collected using a Panalytical Xpert Pro diffractometer equipped with a Cu X-ray tube and a Pixcel detector system. The isothermal samples were analysed in transmission mode and held between low density polyethylene films. The default XRPD program was used (range 3-40° 2θ, step size 0.013°, counting time 99 sec, ~22 min run time).

XRPD data for each of Forms I-IV is provided in Table 2 below.

TABLE 2

| Form I peak positions (2Θ (°)) | Form II peak positions (2Θ (°)) | Form III peak positions (2Θ (°)) | Form IV peak positions (2Θ (°)) |
| --- | --- | --- | --- |
| 7.645 | 3.386 | 5.276 | 3.522 |
| 9.503 | 6.830 | 9.191 | 7.113 |
| 11.281 | 9.059 | 10.627 | 9.428 |
| 13.643 | 10.282 | 14.105 | 12.385 |
| 15.336 | 12.379 | 15.996 | 12.872 |
| 16.344 | 13.743 | 18.499 | 15.609 |
| 18.624 | 14.985 | 19.266 | 16.422 |
| 19.076 | 15.765 | 20.277 | 17.927 |
| 20.744 | 17.215 | 20.985 | 18.644 |
| 21.118 | 18.229 | 21.408 | 20.912 |
| 21.683 | 19.186 | 22.980 | 21.602 |
| 21.864 | 20.513 | 24.212 | 21.837 |
| 22.401 | 20.501 | 25.411 | 22.726 |
| 22.978 | 21.006 | 25.970 | 24.400 |
| 23.806 | 21.728 | 26.505 | 25.967 |
| 23.964 | 21.538 | 27.620 | 27.917 |
| 24.484 | 22.208 | 28.659 | 28.878 |
| 25.456 | 22.733 | 30.127 | 32.684 |
| 25.735 | 23.788 | 31.625 | |
| 26.304 | 24.203 | 34.350 | |
| 27.236 | 24.538 | | |
| 27.639 | 25.274 | | |
| 28.159 | 25.742 | | |
| 28.779 | 26.689 | | |
| 29.502 | 27.228 | | |
| 30.169 | 27.316 | | |
| 30.378 | 28.022 | | |
| 30.656 | 29.333 | | |
| 30.989 | 29.716 | | |
| 31.184 | 30.557 | | |
| 31.559 | 31.784 | | |
| 31.598 | 32.316 | | |
| 32.276 | 33.266 | | |
| 32.557 | 34.364 | | |
| 33.340 | | | |
| 33.843 | | | |
| 34.544 | | | |
| 34.999 | | | |
| 35.521 | | | |
| 35.703 | | | |
| 36.040 | | | |
| 36.920 | | | |
| 37.777 | | | |
| 38.050 | | | |
| 38.218 | | | |
| 38.723 | | | |
| 38.957 | | | |

Preparation of HMPL-504-M2

Step A

Preparation of (S)-tert-butyl 4-(1-(1-(imidazo[1,2-a]pyridin-6-yl)ethyl)-1H-[1,2,3]triazolo[4,5-b]pyrazin-6-yl)-1H-pyrazole-1-carboxylate (Boc-HMPL-504-M2)

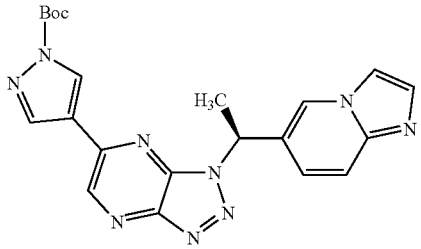

Boc-HMPL-504-M2

To a three-neck RB-flask equipped with a mechanical stirrer, temperature controller, and nitrogen bubbler, was added 50.0 g of crude 5-bromo-3-[(1S)-1-imidazo[1,2-a]pyridin-6-ylethyl]triazolo[4,5-b]pyrazine (VI) (potency assay 70%, 0.15 mol), 67.2 g (0.23 mol, 1.5 eq) of 1-Boc-4-bromo-1H-pyrazole-borate ester, 47.7 g Na$_2$CO$_3$ (0.45 mol, 3 eq), 500 mL of dioxane and 50 mL of water. Nitrogen gas was bubbled into the bottom of the solution to replace the air for 15 min, then 7.7 g of PdCl$_2$(dppf) (0.07 eq) was added, and the whole process was protected with nitrogen. The reaction mixture was heated to a gentle reflux (90 to 95° C.) and held at this temperature for more than 4 hours until LC-MS (or HPLC) showed the reaction was completed. The reaction mixture was cooled to 50° C. and was filtered through a pad of Celite. The filtrate was concentrated under reduced pressure. DCM (800 mL) was added to the residue, the organic phase was separated and washed with water (200 mL×3). The organic phase was concentrated to 200 mL which was then used in the next step directly.

Step B

Preparation of (S)-1-(1-(imidazo[1,2-a]pyridin-6-yl)ethyl)-6-(1H-pyrazol-4-yl)-1H-[1,2,3]triazolo[4,5-b]pyrazine (HMPL-504-M2)

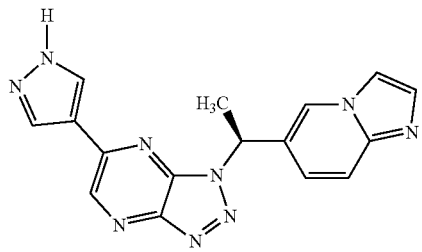

HMPL-504-M2

To the residue obtained from Step A above, 200 mL of dichloromethane was added, followed by concentrated HCl solution (50 mL). The solution was stirred for 4 h, monitored by LC-MS. When the reaction was complete, solvent was removed. To the residue, dilute NaOH solution was added to give a final pH of 7~8. The solid formed was collected by filtration and the crude product was purified by silica gel column chromatography to give 18 g of light yellow solid with a chiral purity of 100% e.e. The chemical purity of the product was 99.03% (HPLC, at 254 nm). The yield was 38% for the Suzuki cross-coupling step and the deprotection step combined.

$^1$H-NMR (DMSO-d$_6$, 400 MHz): δ 13.43 (br, s, 1H), 9.19 (s, 1H), 8.79 (s, 1H), 8.69 (s, 1H), 8.30 (s, 1H), 7.95 (s, 1H), 7.52 (d, J=11.3 Hz, 2H), 7.35 (dd, J=9.4, 1.5 Hz, 1H), 6.39 (q, J=7.0 Hz, 1H), 2.15 (d, J=7.1 Hz, 4H).

$^{13}$C-NMR (DMSO-d$_6$, 100 MHz): δ 148.77, 147.56, 144.28, 142.64, 138.91, 137.78, 134.15, 129.98, 125.92, 124.69, 124.33, 119.26, 117.52, 114.17, 55.87, 19.98.

LC-MS: Calcd for C$_{16}$H$_{13}$N$_9$ (M+H) 332.33, found 332.30.

Preparation of Savolitinib Film-Coated Tablets

An example composition of a savolitinib film-coated tablet is shown in Table 3 below.

TABLE 3

| Components | Quantity wt % of coated tablet |
|---|---|
| Tablet core | |
| Savolitinib | 30-45 |
| Mannitol | 20-40 |

TABLE 3-continued

| Components | Quantity wt % of coated tablet |
|---|---|
| Microcrystalline cellulose | 20-40 |
| Low-substituted hydroxypropyl cellulose | 3-6 |
| Magnesium stearate | 0.5-2.5 |
| Core tablet weight | 95-98 |
| Tablet coating | |
| Hydroxypropyl methylcellulose | 3 |
| Titanium dioxide | 1 |
| Polyethylene glycol 400 | 0.6 |
| Yellow iron oxide | 0.1 |
| Red iron oxide | 0.0004 |
| Black iron oxide | 0.0004 |
| Purified water | qs |
| Nominal coated tablet weight | 100 |

Savolitinib film-coated tablets are manufactured using blending, dry granulation, compression and film coating techniques known to those skilled in the art. The manufacturing process comprises the following steps:

1. The following ingredients are added to a suitable diffusion mixer; savolitinib, mannitol, microcrystalline cellulose and low substituted hydroxypropyl cellulose. The ingredients are then mixed together.
2. Intragranular magnesium stearate is added to the powders, and mixed prior to roller compaction.
3. Ribbons are produced by roller compacting the lubricated blend. Subsequently the ribbons are milled into granules by passing the ribbons through a suitable mill.
4. The granules are mixed with extragranular magnesium stearate using a suitable diffusion mixer.
5. The lubricated granules are compressed into tablet cores using a suitable tablet press.
6. The film-coating suspension is prepared and the tablet cores are coated with a yellow film-coat, which is applied to the tablet cores using a conventional film coating process.
7. The finished coated tablets are packed in appropriate bulk or primary pack.

The invention claimed is:

1. A process for the preparation of Savolinitib (I)

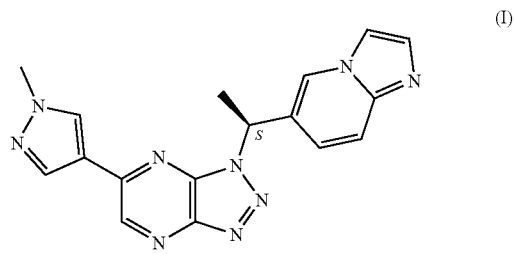

comprising the preparation of (1S)-1-imidazo[1,2-a]pyridin-6-ylethanamine (III),

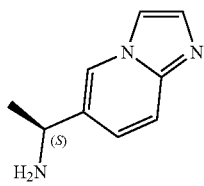

(III)

or a pharmaceutically acceptable salt thereof, comprising the steps of (i) asymmetric enzymatic transamination of 1-imidazo[1,2-a]pyridin-6-ylethanone (II),

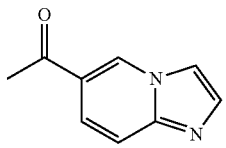

(II)

in the presence of an amine transaminase, pyridoxal phosphate, and an amine source; and (ii) isolation of (1S)-1-imidazo[1,2-a]pyridin-6-ylethanamine (III), or a pharmaceutically acceptable salt thereof.

2. A process according to claim 1 wherein, in step (i), the amine transaminase is ATA-436 and the amine source is isopropylamine hydrochloride.

3. A process according to claim 1, wherein step (i) is carried out at 44-54° C.

4. A process for the preparation of Savolinitib (I) according to claim 1, wherein the process additionally comprises the preparation of 5-bromo-$N_3$-[(1S)-1-imidazo[1,2-a]pyridin-6-ylethyl]pyrazine-2,3-diamine (V),

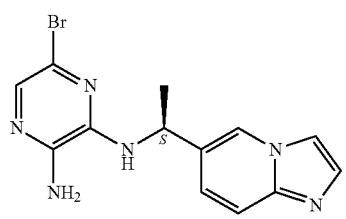

(V)

comprising the steps of (iii) neutralising a pharmaceutically acceptable salt of (1S)-1-imidazo[1,2-a]pyridin-6-ylethanamine (III) with a neutralising agent; followed by (iv) the reaction of (1S)-1-imidazo[1,2-a]pyridin-6-ylethanamine (III) with 3,5-dibromopyrazin-2-amine (IV),

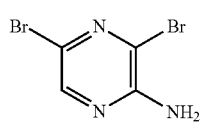

(IV)

in the presence of an organic base; and isolating 5-bromo-$N_3$-[(1S)-1-imidazo[1,2-a]pyridin-6-ylethyl]pyrazine-2,3-diamine (V).

5. A process according to claim 4, wherein step (iv) is carried out in a suitable solvent selected from iso-amyl alcohol and N-methyl-2-pyrrolidone and the organic base is N,N-diisopropylethylamine.

6. A process for the preparation of Savolinitib (I) according to claim 1, wherein the process additionally comprises the preparation of 5-bromo-3-[(1S)-1-imidazo[1,2-a]pyridin-6-ylethyl]triazolo[4,5-b]pyrazine (VI),

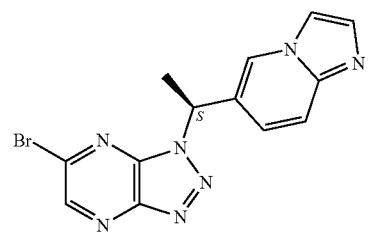

(VI)

or a pharmaceutically acceptable salt thereof, comprising the steps of (v) cyclisation of 5-bromo-$N_3$-[(1S)-1-imidazo[1,2-a]pyridin-6-ylethyl]pyrazine-2,3-diamine (V), in the presence of sodium nitrite under acidic conditions in an aqueous system; and (vi) isolating 5-bromo-3-[(1S)-1-imidazo[1,2-a]pyridin-6-ylethyl]triazolo[4,5-b]pyrazine (VI), or a pharmaceutically acceptable salt thereof.

7. A process according to claim 6, wherein in step (v), the acidic conditions comprise carrying out the reaction in a mixture of acetic acid and water.

8. A process according to claim 6, wherein, in step (vi) 5-bromo-3-[(1S)-1-imidazo[1,2-a]pyridin-6-ylethyl]triazolo[4,5-b]pyrazine (VI) is isolated as a hydrochloride salt from ethyl acetate and wherein step (vi) is carried out at less than 25° C.

9. A process for the preparation of Savolinitib (I) according to claim 1, wherein the process additionally comprises the steps of (vii) the reaction of 5-bromo-3-[(1S)-1-imidazo[1,2-a]pyridin-6-ylethyl]triazolo[4,5-b]pyrazine (VI), or a pharmaceutically acceptable salt thereof, with 1-methyl-4-(4,4,5,5-tetramethyl-1,3,2-dioxaborolan-2-yl)pyrazole (VII),

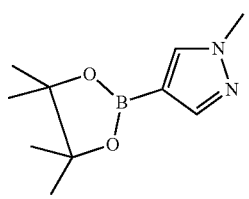

(VII)

in the presence of a palladium catalyst and a suitable base; (viii) treating crude 3-[(1S)-1-imidazo[1,2-a]pyridin-6-ylethyl]-5-(1-methylpyrazol-4-yl)triazolo[4,5-b]pyrazine with a palladium scavenger;
(ix) isolating crude 3-[(1S)-1-imidazo[1,2-a]pyridin-6-ylethyl]-5-(1-methylpyrazol-4-yl)triazolo[4,5-b]pyrazine following azeotropic distillation; and
(x) isolating Savolinitib (I).

10. A process according to claim 9 wherein, in step (vii), the palladium catalyst is Pd(AmPhos)$_2$Cl$_2$ (Pd-132; dichlorobis[di-tert-butyl(4-dimethylaminophenyl)phosphine]palladium(II)) and the suitable base is K$_2$CO$_3$.

11. A process according to claim 9 wherein, in step (viii), the palladium scavenger is L-cysteine.

12. A process according to claim 9 wherein, in step (ix), the azeotropic distillation is carried out using anisole.

13. A process according to claim 9 wherein, in step (x), Savolitinib (I) is isolated from 95:5% v/v ethanol:water in the presence of activated carbon.

* * * * *